US007015309B1

(12) United States Patent
Otvos

(10) Patent No.: US 7,015,309 B1
(45) Date of Patent: Mar. 21, 2006

(54) PYRRHOCORICIN-DERIVED PEPTIDES, AND METHODS OF USE THEREOF

(75) Inventor: Laszlo Otvos, Audubon, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 371 days.

(21) Appl. No.: 09/980,804

(22) PCT Filed: Jun. 21, 2000

(86) PCT No.: PCT/US00/16989

§ 371 (c)(1),
(2), (4) Date: Dec. 3, 2001

(87) PCT Pub. No.: WO00/78956

PCT Pub. Date: Dec. 28, 2000

Related U.S. Application Data

(60) Provisional application No. 60/154,135, filed on Sep. 15, 1999, provisional application No. 60/140,606, filed on Jun. 23, 1999.

(51) Int. Cl.
*C07K 1/00* (2006.01)

(52) U.S. Cl. .................. 530/350; 530/350; 530/300; 514/2; 514/12; 514/21; 435/7.1; 435/69.1; 435/117; 435/129; 424/9.361

(58) Field of Classification Search ............... 530/350, 530/300; 514/2, 12, 21; 435/7.1, 117, 129, 435/69.1; 424/9.361
See application file for complete search history.

(56) References Cited

U.S. PATENT DOCUMENTS

| 5,466,671 | A | 11/1995 | Tempst et al. |
| 5,874,411 | A | 2/1999 | Srivastava |
| 6,001,823 | A | 12/1999 | Hultgren |
| 6,127,336 | A | 10/2000 | Bulet |
| 6,331,522 | B1 | 12/2001 | Bulet |

FOREIGN PATENT DOCUMENTS

| EP | 352014 A2 | 1/1990 |
| FR | 2695392 A1 | 3/1994 |
| FR | 2732345 | 10/1996 |
| FR | 2733237 A1 | 10/1996 |
| WO | WO-93/14118 | 7/1993 |
| WO | WO94/05787 A1 | 3/1994 |
| WO | WO 94/05787 | * 9/1994 |
| WO | WO-94/25616 | 11/1994 |
| WO | WO-96/36707 | 11/1996 |
| WO | WO-96/40928 | 12/1996 |
| WO | WO97/30082 A2 | 8/1997 |
| WO | WO-98/39011 | 9/1998 |
| WO | WO98/40401 A3 | 9/1998 |
| WO | WO99/05270 A2 | 2/1999 |
| WO | WO-00/78956 | 12/2000 |

OTHER PUBLICATIONS

Wells, Biochemistry, vol. 29, pp. 8509-8517, 1990.*
Jones, Science, vol. 302, pp. 1347-1348, 2003.*
(A translation of WO 94/05787 will be provided via fax).*
L. Otvos, et al., "Antibacterial insect glycopeptides: Synthesis, structure and activity", *In: Peptides:* Frontiers in Peptide Science (J.P. Tam and P.T.P. Kaumaya, ed.) Kluwer, Dordrecht, The Netherlands, pp. 703-704 (Jan. 1999).
M. Cudic, et al., "Fully solid-phase synthesis and antimicrobial properties of a cyclic analog of pyrrhocoricin", *In: Peptides 2000* (J. Martinez, J.A.Fehrentz, eds.) EDK, Paris pp. 203-204 (2001).
L. Otvos, et al., "In vivo active antibacterial peptides and their bacterial target proteins", *In: Peptides 2000* (J. Martinez, J.A. Fehrentz, eds.) EDK, Paris pp. 115-116 (2001).
M. Cudic, et al., "Antibacterial activity spectrum of designed pyrrhocoricin analogs", *In Peptides: The Wave of the Future* (R.A. Houghten and M. Lebl, eds.), American Peptide Society, San Diego, pp. 493-494 (2001).
L. Otvos, et al., "The proline-rich antibacterial peptide family inhibits chaperone-assisted protein folding", *In Peptides: The Wave of the Future* (R.A. Houghten and M. Lebl, eds.), American Peptide Society, San Diego, pp. 873-875 (2001).
M. Cudic, et al., "Derivatives of the native antibacterial peptide pyrrhocoricin exhibit desirable pharmacological properties in vitro and in vivo", *In: Peptides 2002* (E. Benedetti and C. Pedfone, eds), Edizioni Ziino, Napoli, pp. 452-453 (2002).
L. Otvos, et al., "Multifunctional antibacterial peptides", *In: Peptides 2002* (E. Benedetti and C. Pedone, eds), Edizioni Ziino, Napoli, pp. 580-581 (2002).
L. Otvos, "Antibacterial peptides isolated from insects", *J. Pept. Sci.* 6:497-511 (Oct. 6, 2000).
M. Cudic, et al., "Intracellular targets of antibacterial peptides", *Curr. Drug Targets* 3(2):101-106 (Apr. 2002).
L. Otvos, "The short, proline-rich antibacterial peptide family", *Cell. Mol. Life Sci.,* 59:1138-1150 (Jul. 2002).

(Continued)

*Primary Examiner*—Jon Weber
*Assistant Examiner*—Hope Robinson
(74) *Attorney, Agent, or Firm*—Howson and Howson

(57) ABSTRACT

Modifications of the peptide pyrrhocoricin permit the production of a variety of anti-bacterial or anti-fungal peptides having general formula $R^1$-Asp-Lys-Gly-X-Y-Leu-Pro-Arg-Pro-Thr-Pro-Pro-Arg-Pro-Ile-Tyr-X'-Y'-$R^2$ SEQ ID NO: 1 or multimeric compositions containing more than a single peptide of that formula. These peptides may be straight chain or cyclic peptides, and may contain one or more non-cleavable bonds. These peptides are characterized by anti-bacterial or anti-fungal activity and metabolic stability in mammalian serum. These peptides are useful in anti-bacterial or anti-fungal pharmaceutical compositions and for further drug development or identification of other antibiotic or anti-fungal compounds.

55 Claims, 3 Drawing Sheets

OTHER PUBLICATIONS

P. Bulet, et al., "Enlarged scale chemical synthesis and range of activity of drosocin, an O-glycosylated antibacterial peptide of Drosophila", Eur. J. Biochem. 238:64-69 (May 15, 1996).

R. Hoffman, et al., "Serum stability of phosphopeptides", Anal. Chim. Acta 352:319-325 (1997).

M. Cudic, et al., "Chemical synthesis, antibacterial activity and conformation of diptericin, an 82-mer peptide originally isolated from insects", Eur. J. Biochem. 266:549-558 (Dec. 1999).

L. Otvos, et al., Insect peptides with improved protease-resistance protect mice against bacterial infection, Protein Sci. 9:742-749 (Apr. 2000).

G. Kragol, et al., "The antibacterial peptide pyrrhocoricin inhibits the ATPase actions of DnaK and prevents chaperone-assisted protein folding", Biochemistry 40:3016-3026 (Mar. 13, 2001).

A.M. Bencivengo, et al., "The efficacy of the antibacterial peptide, pyrrhocoricin, is finely regulated by its amino acid residues and active domains", Lett. Pept. Sci. 8: 201-209 (2002).

G. Kragol, et al., "Identification of crucial residues for the antibacterial activity of the proline-rich peptide, pyrrhocoricin", Eur. J. Biochem. 269: 4226-4237 (Sep. 2002).

M. Cudic, et al., "Development of novel antibacterial peptides that kill resistant clinical isolates", In: Peptides 23: 2071-2083 (Dec. 2002).

M. Cudic, et al., "In vitro and in vivo activity of an antibacterial peptide analog against uropathogens", In: Peptides, in press. (2003).

S. Bajusz & F. Hudecz (ed.), Peptides 1998, Proceedings of the European Peptide Symposium, 25th, Aug. 30-Sep. 4, 1998, pp 786-787.

B. Weinstein, "Chemistry and Biochemistry of Amino Acids, Peptides and Proteins", Marcel Dekker, Inc., New York and Basel. pp 267-387 (1982).

R. Hoffmann et al, "Range of Activity and Metabolic Stability of Synthetic Antibacterial Glycopeptides from Insects", Biochimica et Biophysica Acta, 1426:459-467 (Feb., 1999).

A. McManus et al, "Conformational Studies by NMR of the Antimicrobial Peptide, Drosocin and its Non-Glycosylated Derivative: Effects of Glycosylation on Solution Conformation", Biochemistry, 38(2):705-714 (1999).

P. Bulet et al, "Enlarged Scale Chemical Synthesis and Range of Activity of Drosocin, an O-glycosylated Antibacterial Peptide of Dropsophila", Eurl J. Biochem., 238:64-69 (1996).

P. Bulet et al, "A Novel Inducible Antibacterial Peptide of Drosophila Carries an O-Glycosylated Substitution", J. Biol. Chem., 268(20):14893-14897 (Jul., 1993).

S. Cociancich et al, "Novel Inducible Antibacterial Peptides from a Hemipteran Insect, the sap-sucking bug Pyrrhocoris apterus", Biochem. J., 300:567-575 (1994).

D. Hultmark, "Immune Reactions in Drosophila and Other Insects: A Model for Innate Immunity", Trends Genet., 95(5):178-183 (May, 1993).

J. Gillespie et al, "Biological Mediators of Insect Immunity", Annu. Rev. Entomol., 42:611-643 (1997).

L. Otvos et al, "Insect Peptides with Improved Protease-Resistance Protect Mice Against Bacterial Infection", Protein Science, 9:742-749 (2000).

Adcock et al., "Methicillin-Resistant Staphylococcus aureus in Two Child Care Centers", Journal of Infectious Diseases, Aug. 1998, 178:577-580.

Andreu et al., "Animal Antimicrobial Peptides: An Overview", Biopolymers (Peptide Science), May 1998, 47: 415-433.

Bulet et al., "Antimicrobial peptides in insects; structure and function", Dev. Comp. Immunol., Jun-Jul. 1999, 23(4-5): 329-344.

Casteels et al., "Apidaecin-Type Peptide Antibiotics Function Through a Non-Poreforming Mechanism Involving Stereospecificity", Biochemical and Biophysical Research Communications, Feb. 1994, 199(1):339-345.

Castle et al., "Lethal Effects of Apidaecin on Escherichia coli Involve Sequential Molecular Interactions with Diverse Targets", Journal of Biological Chemistry, Nov. 1999, 274 (46):32555-32564.

Cociancich et al., "The inducible antibacterial peptides of insects", Parasitol. Today, Apr. 1994, 10(4):132-139.

Giglione et al., "Peptide Deformylase as a Target for New Generation, Broad Spectrum Antimicrobial Agents", Molecular Microbiology, Jun. 2000, 36(6):1197-1205.

Kabsch et al., "Dictionary of Protein Secondary Structure: Pattern Recognition of Hydrogen-Bonded and Geometrical Features", Biopolymers, Dec. 1983, 22:2577-2637.

Liang et al., "Not Only the Nature of Peptide but Also the Characteristics of Cell Membrane Determine the Antimicrobial Mechanism of a Peptide", Journal of Peptide Research, May 1999, 53(5):518-522.

Maguire et al., "Clinical Experience and Outcomes of Community-Acquired and Nosocomial Methicillin-Resistant Staphylococcus aureus in a Northern Australian Hospital", Journal of Hospital Infection, Apr. 1981, 38:273-281.

Moellering, "Emerging Resistance with Gram-Positive Aerobic Infections: Where Do We Go From Here?", Clinical Infectious Diseases, May 1998, 26:1177-1178.

Otvos et al., "Interaction Between Heat Shock Proteins and Antimicrobial Peptides", Biochemistry, Mar. 2000, 39(46): 14150-14259.

Park et al., "Mechanism of Action of the Antimicrobial Peptide Buforin II: Buforin II Kills Microorganisms by Penetrating the Cell Membrane and Inhibiting Cellular Functions", Biochemical and Biophysical Research Communications, Mar. 1998, 244(1):253-257.

Spatola, "Peptide Backbone Modifications: A Structure-Activity Analysis of Peptides Containing Amide Bond Surrogates", Chemistry and Biochemistry of Amino Acids, Peptides and Proteins, 1982, vol. 7, Chapter 5, pp. 267-357, Weinstein, Ed., Marcel Dekker, Inc., New York, New York.

Stephen et al., Direct Submission, Database NCBI, Accession No. Q56073, Nov. 1997.

Tan et al., "Molecular Strategies for Overcoming Antibiotic Resistance in Bacteria", Molecular Medicine Today, Aug. 2000, 6:309-314.

Tomasz, "Multiple-Antibiotic-Resistant Pathogenic Bacteria—A Report on the Rockefeller University Workshop", New England Journal of Medicine, Apr. 1994, 330(17):1247-1251.

Wang et al., "NMR Solution Structure of the 21 kDa Chaperone Protein DnaK Substrate Binding Domain: A Preview of Chaperone-Protein Interaction", Biochemistry, May 1998, 37(22):7929-7940.

Zhu et al., "Structural Analysis of Substrate Binding by the Molecular Chaperone DnaK", Science, Jun. 1996, 272 (5268):1606-1619.

European Office Action from corresponding European Patent Application No. 00946829.9, dated Mar. 19, 2004.

* cited by examiner

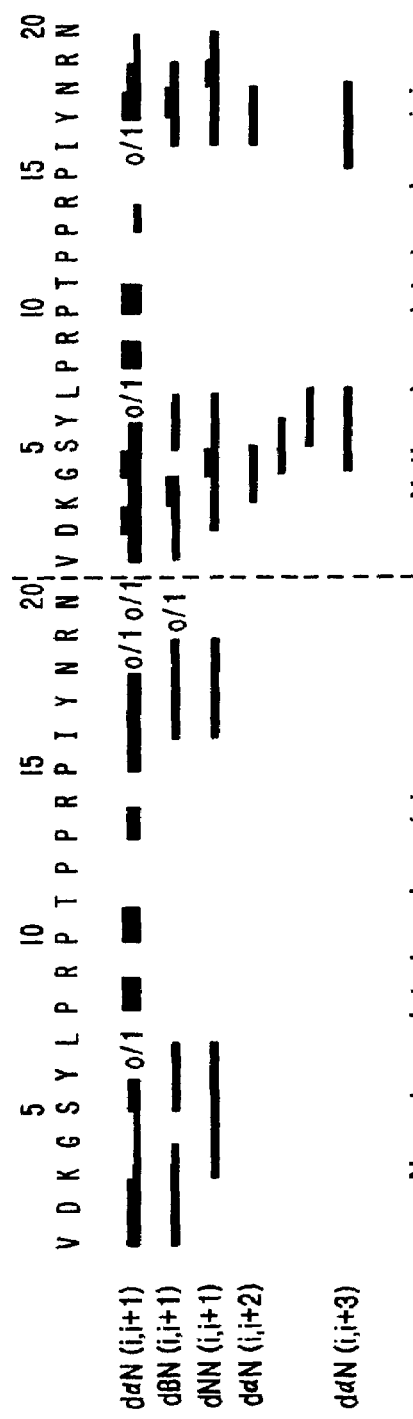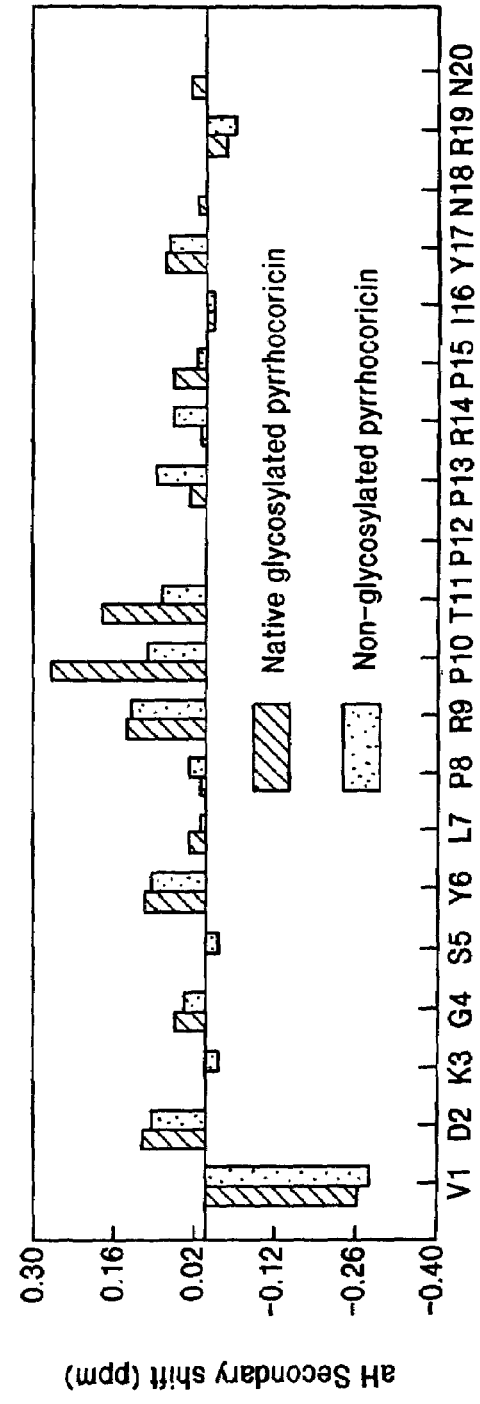
FIG. 3A
FIG. 3B
FIG. 3C

PYRRHOCORICIN-DERIVED PEPTIDES, AND METHODS OF USE THEREOF

"This application is a 371 of PCT/US00/16989, filed Jun. 21, 2000, which claims benefit of U.S. Provisional Application No. 60/154,135, filed Sep. 15, 1999 and U.S. Provisional Application No. 60/140,606, filed Jun. 23, 1999.

This invention was supported in part by National Institute of Health grant Nos. GM45011. The United States government has an interest in this invention.

FIELD OF THE INVENTION

The invention relates generally to novel peptides; more specifically, the invention relates to compositions and methods for killing bacteria or fungus or treating bacterial, fungal or other microbial infections with pyrrhocoricin-based peptides.

BACKGROUND OF THE INVENTION

In the continuing search for new compounds that can break drug resistance in bacterial infections of humans and other mammalian species, certain anti-bacterial peptides and glycopeptides isolated from insects have been noted as promising candidates for drug development [D. Hultmark, *Trends Genet.*, 9:178–183 (1993); J. P. Gillespie et al, *Annu. Rev. Entomol.*, 42:611–643 (1997)]. See, also, International Patent Application No. WO94/05787, published Mar. 17, 1999; French patent No. 2733237, granted Oct. 25, 1996; International Patent Application No. WO99/05270, published Feb. 4, 1999; International Patent Application No. WO97/30082, published Aug. 21, 1997; French patent No. 2695392 granted Mar. 11, 1994 and French patent No. 2732345, granted Oct. 4, 1996.

While many anti-bacterial peptides from other origins kill bacteria by disrupting the cell membrane or cell wall, some of the insect-derived anti-bacterial peptides have an unusual mode of action, i.e., they bind to a currently unknown, stereospecific target molecule [P. Bulet et al, *Eur. J. Biochem.*, 238:64–69 (1996)]. Two such peptides are drosocin, a 19 amino acid residue peptide from species of *Drosophila* [P. Bulet et al, *J. Biol. Chem.*, 268(20):14893–14897 (1993)] and pyrrhocoricin, a 20 amino acid residue peptide from species of *Pyrrhocoris* [S. Cociancich et al, *Biochem, J.*, 300:567–575 (1994)]. Drosocin and pyrrhocoricin are glycopeptides characterized by the presence of a disaccharide in the mid-chain position. The presence of the sugar increases the in vitro anti-bacterial activity of drosocin, but decreases the activity of pyrrhocoricin [P. Bulet et al, 1996, cited above; R. Hoffmann et al, *Biochim. et Biophys. Acta*, 1426: 459–467 (1999)].

Drosocin is moderately active against Gram-positive bacteria. When the native glycosylated drosocin is injected into mice, the glycopeptide shows no anti-bacterial activity, probably due to the peptide's rapid decomposition in mammalian sera [Hoffmann et al, 1999, cited above]. While drosocin needs 12–24 hours to kill bacteria in vitro, it is completely degraded in diluted human and mouse serum within a four-hour period. Both aminopeptidase and carboxypeptidase cleavage pathways (decomposition at both ends) can be observed.

Native pyrrhocoricin is also a glycosylated peptide. Pyrrhocoricin is more active against Gram-negative bacteria than drosocin, but the peptide is almost completely inactive against Gram-positive strains. Native pyrrhocoricin appears to be more resistant to mouse serum degradation than drosocin, but decomposes quickly in some batches of human serum.

Metabolites from serum stability assays of drososin and pyrrhocoricin were identified, and the metabolites, lacking as few as five amino terminal or two carboxy terminal amino acids are inactive [Bulet et al, 1996 and Hoffmann et al, 1999, both cited above). This is further supported by a recent model of the bioactive secondary structure of drosocin, which identifies two reverse turns, one at each terminal region, as binding sites to the target molecule [A. M. McManus et al, *Biochem.*, 38(2):705714 (1999)]. The situation is further complicated by the fact that the degradation speed and pathway of a given peptide in diluted mouse sera are somewhat different from those observed in diluted human sera. Even different batches of human sera degrade the peptides at different rates and may yield different metabolites in vitro. The peptide's stability is markedly increased in insect hemolymph where the peptides manifest their biological functions [Hoffmann et al, 1999, cited above].

There exists a need in the art for novel anti-bacterial and anti-fungal compounds, novel anti-bacterial and anti-fungal pharmaceutical compositions and methods of use thereof, and novel compounds which can be employed in drug screening analyses to detect new pharmaceutical antibiotics.

SUMMARY OF THE INVENTION

In one aspect, the invention provides a modified peptide which has anti-bacterial or anti-fungal activity, and has the formula:

$R^1$-Asp-Lys-Gly-X-Y-Leu-Pro-Arg-Pro-Thr-Pro-Pro-Arg-Pro-Ile-Tyr-X'-Y'-$R^2$ ($R^1$-SEQ ID NO: 1-$R^2$), wherein $R^1$ is a moiety having a net positive charge;

wherein $R^2$ is selected from the group consisting of a free hydroxyl, an amide, an imide, a sugar and a sequence of one or up to about 15 additional amino acids, optionally substituted with a free hydroxyl, an amide, an imide or a sugar. These additional amino acids are independently selected from L-configuration or D-configuration. These additional amino acids may be capable of forming a cyclic peptide by linkage to the N-terminal amino acid. Such an amino acid may be modified by the insertion of a sugar, imide groups and the like. These additional amino acids may also form spacers to cyclize the peptide by bridging between the N- and C-termini of the peptide;

wherein X and Y form a dipeptide, which is Ser-Tyr or is a dipeptide formed of naturally occurring amino acids or unnatural amino acids, the dipeptide being resistant to cleavage by endopeptidases; and wherein X' and Y' form a dipeptide, which is Asn-Arg, or is a dipeptide formed of naturally occurring amino acids or unnatural amino acids, the dipeptide being resistant to cleavage by endopeptidases. In one preferred embodiment, this peptide is a cyclic peptide in which $R^1$ and/or $R^2$ form an amino acid spacer (which is preferably a sequence duplicating at least a portion of the pyrrhocoricin peptide) linking the N- and C-terminal amino acids of the above formula. The peptides of this formula include modified peptides in which one or more conventional amide bonds between amino acids is replaced with a bond resistant to a protease, such as a thio-amide bond or a reduced amide bond. Further a variety of multimeric peptide constructs are included in this invention.

In a further aspect, the invention provides a composition comprising multiple peptides of the formula above in a variety of multimeric constructs. Such compositions containing one or more peptides of this invention may optionally contain a pharmaceutically acceptable carrier.

In another aspect, the invention provides an isolated nucleic acid molecule comprising a nucleotide sequence encoding the anti-bacterial or anti-fungal peptide or multimeric compositions of the invention in operative association with a regulatory sequence directing the expression thereof in a host cell. In yet a further aspect, the invention provides a host cell transfected or transformed with the above-described nucleic acid molecule.

In another aspect, the invention provides a method of treating a mammalian bacterial or fungal infection comprising administering to a mammal having said infection an effective anti-bacterial or anti-fungal amount of a pharmaceutical composition described herein.

In yet another aspect, the invention provides a method for designing antibacterial or anti-fungal pharmaceutical compounds. In one embodiment, this method employs a peptide or multimeric construct described herein in a computer modeling program to design a compound which mimics the structure and biological effect of said peptide. In another embodiment, the method employs a peptide or multimeric construct described herein in an assay or computer program for identifying the peptide's receptor on a selected bacterium.

In another aspect the invention provides a screening method for identifying test compounds which compete with the peptides or multimeric compositions of this invention for binding to the unknown receptor on the pathogen. Thereafter, test compounds which compete with the peptides or multimeric constructs of this invention for the receptor are identified and screened for anti-bacterial or anti-fungal use.

In yet a further aspect, the invention provides novel compositions identified or produced by the methods described above.

Other aspects and advantages of the present invention are described further in the following detailed description of the preferred embodiments thereof.

Figure 1:
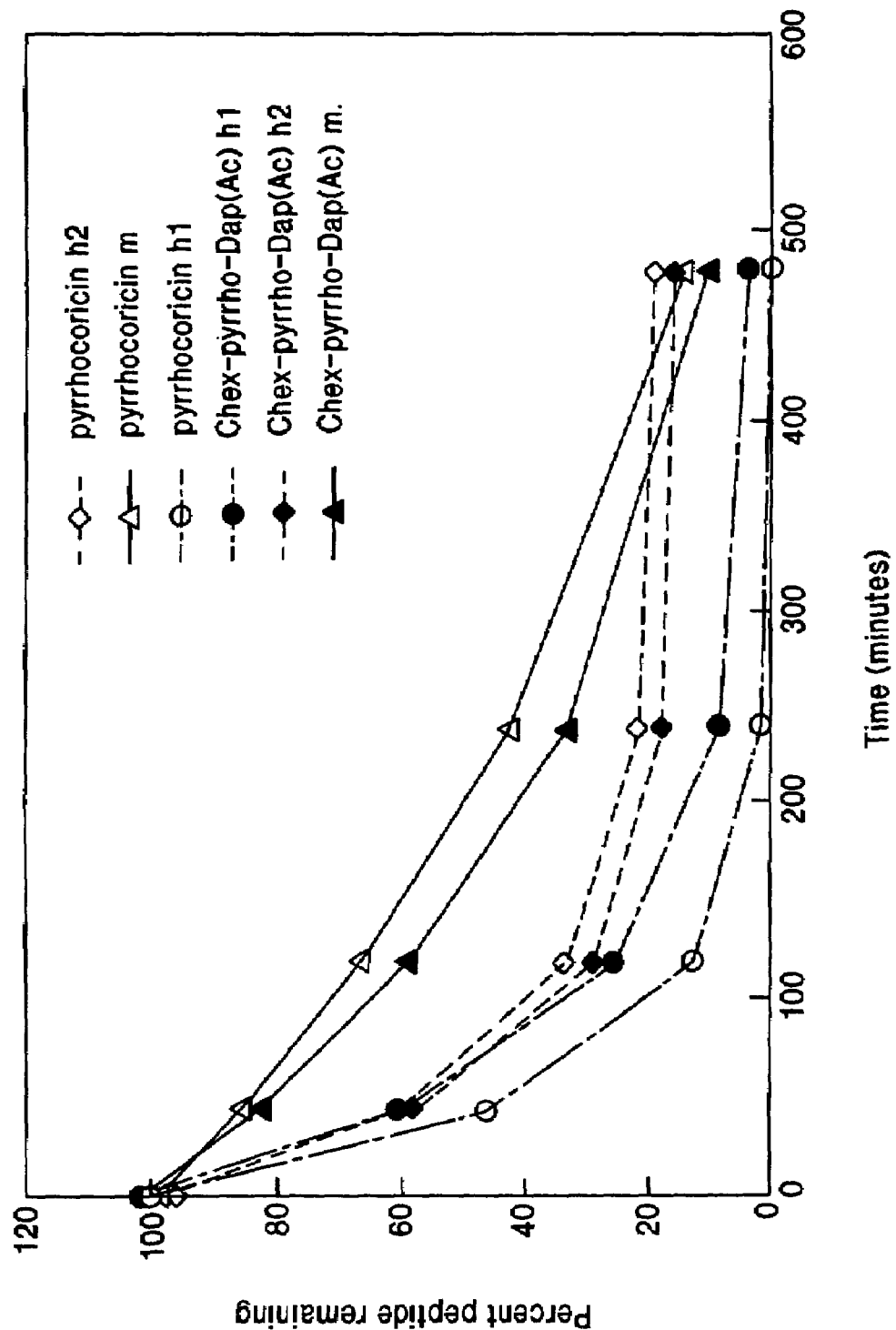
FIG. 1 is a graph illustrating the degradation of deglycosylated pyrrhocoricin (Peptide # 1) and a modified pyrrhocoricin peptide of this invention, i.e., 1-aminocyclohexane carboxylic acid (Chex)-Pyrrhocoricin-β-acetyl-2,3-diamino propionic amide [Dap(Ac)] (Peptide #21) in 25% mammalian sera over time. The different symbols illustrate the pyrrhocoricin or modified peptide in mouse sera (m), in year-old human sera (h1) and in the month-old human sera (h2). The modified peptide is described in detail below in Example 1. The degradation assay is described below in Example 4.

--○-- for 50 mg/kg pyrrhocoricin, toxicity assay control;

--●-- for 50 mg/kg Chex-pyrrhocoricin-Dap(Ac), toxicity assay control;

-|-- for *E. coli* infection, no peptide, as a positive control for infection;

▲ for 10, 25, and 50 mg/kg Chex-pyrrhocoricin-Dap(Ac) as test peptides after infection;

▽ for 50 mg/kg pyrrhocoricin as test peptide after infection; and

Δ for 10, 25 mg/kg pyrrhocoricin as a test peptide after infection.

FIG. 3A is a summary of NOE connectivities for deglycosylated pyrrhocoricin. The intensities are indicated by the thickness of the line.

FIG. 3B is a summary of NOE connectivities for the native pyrrhocoricin containing a Gal-GalNAc disaccharide moiety of Thr 11 (Peptide #2). The intensities are indicated by the thickness of the line.

FIG. 3C is a graph showing the deviations from the αH chemical shifts from their "random coil" values for deglycosylated pyrrhocoricin (Peptide #1), indicated as a black bar, and for its native counterpart, containing a Gal-GalNAc disaccharide moiety of Thr 11 (Peptide #2), indicated by a striped bar. The random coil values are corrected for sequence specific shift of 0.29 ppm for residues preceding Pro.

DETAILED DESCRIPTION OF THE INVENTION

The present invention provides modified peptides and multimeric compositions of such peptides having anti-bacterial or anti-fungal activity. The peptides are structurally based on the naturally occurring glycosylated peptide, pyrrhocoricin. The peptides and/or multimeric peptide constructs of this invention, which are modified to delete the mid-peptide glycosylation, are characterized by the high anti-bacterial or anti-fungal potency in vitro of the unmodified pyrrhocoricin peptide, and provide good metabolic stability in mammalian serum.

A. Peptides of the Invention

According to this invention, preferred anti-bacterial or anti-fungal peptides based on pyrrhocoricin are defined by the following formula $R^1$-Asp-Lys-Gly-X-Y-Leu-Pro-Arg-Pro-Thr-Pro-Pro-Arg-Pro-Ile-Tyr-X'-Y'-$R^2$ [SEQ ID NO: 1]. As used in the above formula, the N-terminal $R^1$ is any moiety which can provide a net positive charge on the N-terminus of the modified peptide.

Thus, for example, $R^1$ may be selected from one or more of the following groups:

(a) a straight chain, branched, cyclic or heterocyclic alkyl group, (b) a straight chain, branched, cyclic or heterocyclic alkanoyl group, (c) a positively charged reporter group; and/or (d) one or up to 15 additional amino acids independently selected from L-configuration or D-configuration amino acids, optionally substituted with a straight chain, branched, cyclic or heterocyclic alkyl group, a straight chain, branched, cyclic or heterocyclic alkanoyl group, or a reporter group. The amino acids may be naturally occurring amino acids or unnatural amino acids, such as D configuration amino acids, or amino acids which are capable of cyclizing the peptide by attachment to a carboxy terminal amino acid. The amino acid may be further modified by the insertion of modifying sugars, imide groups and the like. These amino acids may also form spacers, as described below, to cyclize the peptide by bridging between the N- and C-termini of the peptide. A variety of methods for producing non-natural amino acids are known and may be selected by one of skill in the art.

In one example of the (a) group above, the positively charged 1-aminocyclo-hexane carboxylic acid (Chex) is employed as $R^1$. In an embodiment of (d), the $R^1$ group is formed by one or more positively charged amino acid residues or amino acid sequences. For example, $R^1$ may be a single positively charged amino acid such as L-Val- or D-Val-. $R^1$ may be a sequence of amino acids with a net positive charge, such as Arg-Val-, Lys-Val-, Lys-Val-Asp-Lys-Val-[SEQ ID NO: 5], and -Arg-Pro-Pro-Thr-Pro-Arg-Pro-Leu-Lys-Val-[SEQ ID NO: 3]. In still other embodiments, such additional amino acids are modified by an acetyl group, providing that a net positive charge results. Some examples of these $R^1$ groups are Acetyl-Arg-Val-; Acetyl-Lys-Val-; and Acetyl-Lys-Val-Asp-Lys-Val-[SEQ ID NO: 29]. Acetylation alone with Val has been found to extinguish the positive charge.

In still other embodiments of peptides falling within this formula, the $R^1$ group is a positively charged moiety which can function as a reporter group (c) for detection purposes. A reporter group may be defined as a moiety which is capable, alone or in concert with other compositions or compounds, of providing a detectable signal. The reporter may be interactive to produce a detectable signal. Most desirably, the reporter is detectable visually, e.g. colorimetrically. A variety of enzyme systems have been described in the art which will operate to reveal a calorimetric signal in an assay. As one example, glucose oxidase (which uses glucose as a substrate) releases peroxide as a product. Peroxidase, which reacts with peroxide and a hydrogen donor such as tetramethyl benzidine (TMB) produces an oxidized TMB that is seen as a blue color. Other reporters include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other reporter molecules that may be utilized in the methods of this invention are biotin-avidin, fluorescent compounds such as fluorescein, green and blue fluorescent proteins; and radioactive compounds or elements, such as radioactive iodine, and the like. For example, in some peptides of this invention the $R^1$ group is the reporter biotin bound to a lysine-valine dipeptide by a covalent bond. Still another peptide of this invention contains a $R^1$ (d) group which is a reporter group covalently bonded to one or more amino acid residues, resulting in a net positive charge, for example, a 5(6) carboxyfluorescein functionalized-Lys-Val-. Such reporters for attachment to the N-termini of the peptides of this invention may be readily selected from among numerous compositions known and readily available to one skilled in the art of diagnostic assays. The above-listed reporters are understood to be nonexclusive.

Still other peptides of this invention are cyclic peptides, and in these peptides, $R^1$ is an amino acid "spacer". Spacers are sequences of greater than 3 amino acids which are interposed between the normal N-terminus and C-terminus of the modified pyrrhocoricin. These spacers permit linkage therebetween without imposing any adverse restraint upon the molecular structure. Spacers may also contain restriction endonuclease cleavage sites to enable separation of the sequences, where desired. Desirably, spacers duplicate a portion of the pyrrhocoricin peptide. Suitable spacers or linkers are known and may be readily designed and selected by one of skill in the art. In one embodiment, an amino acid spacer is greater than 5 amino acid residues in length. In a preferred embodiment, the amino acid spacer is greater than 10 amino acid residues in length. The amino acid residues in the spacer may be a sequence of any natural or unnatural amino acids. In an exemplary spacer, the inventor incorporated a sequence which duplicated part of the native pyrrhocoricin, e.g. -Arg-Pro-Pro-Thr-Pro-Arg-Pro-Leu-Lys-Val-[SEQ ID NO: 3]. The Val in this $R^1$ group is linked to the N-terminal Asp of the formula and the N-terminal amino acid of $R^1$ is linked by a covalent bond to the C-terminal amino acid of $R^2$.

The $R^2$ group of peptides of the above formula may be a free hydroxyl, an amide, an imide, a sugar, or a sequence of one or up to about 15 additional amino acids, optionally substituted with a free hydroxyl, an amide, an imide or a sugar. The amino acids may be naturally occurring amino acids or unnatural amino acids, such as D configuration amino acids. The additional amino acids may be capable of forming a cyclic peptide by attaching to an amino terminal amino acid. These amino acids may also be modified by insertion of a sugar, imide groups and the like. These additional amino acids may also form spacers, as described above for $R^1$, to cyclize the peptide by bridging between the N- and C-termini of the peptide. A variety of methods for producing non-natural amino acids are known and may be selected by one of skill in the art. For example, in some peptides, $R^2$ is D-Asn, L-Asn, Asp, or Asn-$R^3$, wherein $R^3$ is a sugar. In some embodiments $R^3$ is 2-acetamido-2-deoxyglucose; in other preferred embodiments, the $R^3$ is triacetyl 2-acetamido-2-deoxyglucose. In other embodiments of the peptides of this invention $R^2$ is a β-acetyl-2,3-diamino propionic amide group (DAP(Ac)).

In this formula, X-Y represent two adjacent amino acids which are either Ser-Tyr, or are adjacent amino acids which are resistant to cleavage by endopeptidases. In this formula, X'-Y' represent two adjacent amino acids which are Asn-Arg, or are adjacent amino acids which are resistant to cleavage by endopeptidases. Still other peptides according to the above formula are characterized by having at least one, and preferably more, amino acids altered to the corresponding D amino acid.

The peptides of this formula include modified peptides in which the amino acids may be connected by conventional amide bonds. Alternatively, modified peptides include those in which one or more of the natural or unnatural amino acids may be connected by bonds resistant to proteases, such as, a thioamide bond or a reduced amide bond. Such modifications of the bonds between amino acids may change the conformation of the peptide. Other backbone-modifications of these peptides are also anticipated to improve proteolytic stability and yield analogs with slightly modified activity spectrum. Such modifications include those described for another anti-bacterial peptide in J. E. Oh et al, *J. Peptide Res.*, 54:129–136 (1999).

Preferably, one or more of said peptides is a synthetic peptide fused to a second moiety, which moiety enhances the bioavailability of said peptide.

B. Multimeric Compositions of the Invention

In another embodiment, multiple peptides of the formula described above may be organized in multimeric constructs or compositions. For example, optional amino acids (e.g., -Gly-Ser-) or other amino acid or chemical compound spacers may be included at the N- or C-termini of the peptides for the purpose of linking two or more peptides together or to a carrier. This composition may take the form of one or more of the above-described peptides expressed as a synthetic peptide coupled to a carrier protein. Alternatively, a composition may contain multiple peptides, each expressed as a multiple antigenic peptide, optionally coupled to a carrier protein. Alternatively, the selected peptides may be linked sequentially and expressed as a recombinantly produced protein or polypeptide. As one embodiment, multiple peptides are linked sequentially, with protein or other molecule which can enhance the stability of the peptide. One of skill in the art can readily select an appropriate conjugation moiety.

One desirable example of a multimeric composition according to this invention has the structure of a multi-(peptide [SEQ ID NO: 4]) construct as follows:

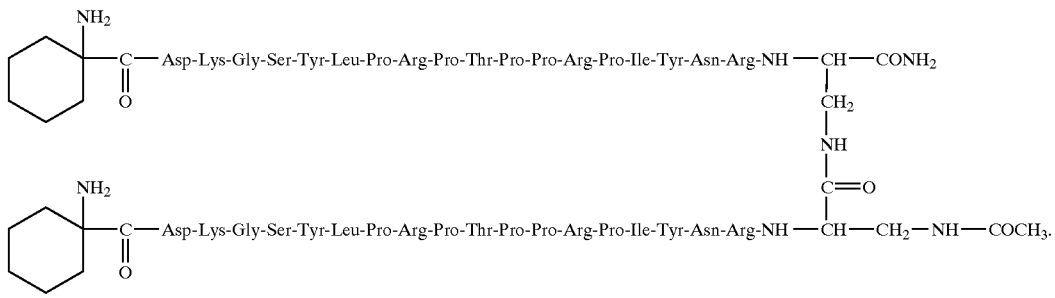

and without spacer amino acids therebetween, to form a larger recombinant protein. Alternatively, the recombinant protein may be fused in frame with a carrier protein.

In one embodiment of a multimeric construct containing at least two of the above-defined peptides (which may be the same or different peptides of the formula), one peptide is attached to any amino acid of the other peptide(s). Any number of additional peptides may be attached to any amino acid of the other peptides in the composition. In another embodiment of a multimeric composition containing at least two peptides, the second or additional peptides are attached to a branched construct of the other peptides in the composition. Alternatively, each additional peptide is covalently linked to $R^2$ of another peptide in the composition.

In another embodiment of a multimeric construct or composition containing at least two of the peptides, at least one or more of the peptides is attached to a carrier. In another embodiment, one or more of said peptides is a synthetic peptide fused to a carrier protein. Still alternatively multiple of the above-described peptides with or without flanking sequences, may be combined sequentially in a polypeptide. The peptides or this polypeptide may be coupled to the same carrier, or different peptides may be coupled individually as peptides to the same or a different immunologically inert carrier proteins.

Suitable carrier proteins may enhance stability or delivery, improve the production, or change the activity spectrum of the peptide. As a few well-known examples, such carrier moieties may be human albumin, polyethylene glycol, other biopolymers or other naturally or non-naturally occurring polymers. In one embodiment, the moiety is desirably a In yet another embodiment, the peptides may be in the form of a multiple antigenic peptide ("MAP"). Such a construct may be designed employing the MAP system described by Tam, *Proc. Natl. Acad. Sci. USA*, 85:5409–5413 (1988). This system makes use of a core matrix of lysine residues onto which multiple copies of the same peptide of the invention are synthesized as described [see, e.g., D. Posnett et al., *J. Biol. Chem.*, 263(4):1719–1725 (1988)]. Each MAP contains multiple copies of one or more of the peptides or this invention. One embodiment of a MAP contains at least three, and preferably four or more peptides. One preferred embodiment contains a β-alanine substituent on the poly-lysine core. One particularly desirable multiple antigenic complex has the formula

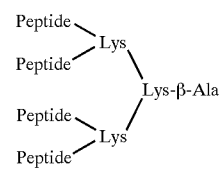

11

In one preferred embodiment of this structure, each peptide is the same and is [SEQ ID NO: 10]:

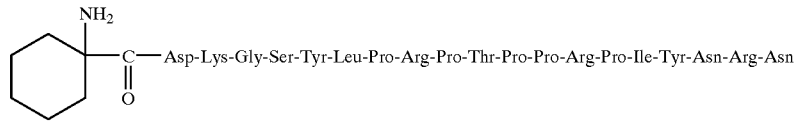

One of skill in the art may readily make any number of multimeric constructs from the peptides of the formula identified above with resort to only conventional skills and knowledge in light of this specification. All such multimeric compositions and constructs are intended to be included in this invention.

C. Methods of Production

Such peptides and multimeric compositions may be produced synthetically or recombinantly by conventional methods. Specific embodiments of pyrrhocoricin-derived antibacterial/anti-fungal peptides of this invention are disclosed in detail in Example 1 below. Preferably, the peptides of the invention are prepared conventionally by known chemical synthesis techniques. Among such preferred techniques known to one of skill in the art are included the synthetic methods described by Merrifield, *J. Amer. Chem. Soc.*, 85:2149–2154 (1963) or as detailed in Example 1.

Alternatively, the peptides or multimeric compositions of this invention may be prepared by known recombinant DNA techniques by cloning and expressing within a host microorganism or cell a DNA fragment carrying a nucleic acid sequence encoding one of the above-described peptides. Coding sequences for these peptides can be prepared synthetically [W. P. C. Stemmer et al, *Gene*, 164:49 (1995)]. Coding sequences can be derived from bacterial RNA by known techniques, or from available cDNA-containing plasmids. Conventional molecular biology techniques, and site-directed mutagenesis may be employed to provide desired peptide sequences. Nucleic acid sequences encoding these peptides may be used in cloning and expressing the peptide compositions of this invention in various host cells well known in recombinant technology, e.g., various strains of *E. coli, Bacillus, Streptomyces,* and *Saccharomyces*, mammalian cells, (such as Chinese Hamster ovary cells (CHO) or COS-1 cells), yeast and insect cells or viral expression systems, such as baculovirus systems. The selection of other suitable host cells and methods for transformation, culture, amplification, screening and product production and purification can be performed by one of skill in the art by reference to known techniques. See, e.g., Gething and Sambrook, *Nature*, :293:620–625 (1981). When produced by conventional recombinant means, the peptides of this invention may be isolated either from the host cell by conventional lysis techniques or from cell medium by conventional methods, such as chromatography. See, e.g., Sambrook et al, *Molecular Cloning. A Laboratory Manual.*, 2d ed., Cold Spring Harbor Laboratory, New York (1989).

The resulting peptide or multimeric construct is screened for antibiotic or antifungal efficacy and/or metabolic stability by in vitro and in vivo assays, such as those described in the examples and in the art. These peptides generally have "significant" metabolic stability in mammalian serum, i.e., the peptides are stable for at least 2 hours in serum. More preferred peptides are stable for at least 4 hours in serum. Still more preferred peptides of this invention are stable in serum for greater than 8 hours.

D. Pharmaceutical Compositions of the Invention and Methods of Treatment

The compositions of this invention are designed to treat infection by the selected bacterium or fungus of an infected mammal, e.g., human. At least one, or alternatively, several of the peptides or multimeric constructs of the present invention may be formulated into an anti-bacterial or anti-fungal composition with a pharmaceutically acceptable carrier and other optional components. For use in such compositions, the selected peptide may be produced preferably synthetically, but also recombinantly, as disclosed above.

The peptides may be employed in pharmaceutical compositions individually. Alternatively, for the purposes of enhancing pharmacokinetics or bioavailability without eliciting immune responses, one or more peptides may be fused or conjugated to other moieties as described above. Any number of single peptides or multimeric constructs may be mixed together to form a single composition.

As pharmaceutical compositions, these compositions are admixed with a pharmaceutically acceptable vehicle or carrier suitable for administration as a protein composition. These peptides may be combined in a single pharmaceutical preparation for administration. Suitable pharmaceutically acceptable carriers for use in a pharmaceutical proteinaceous composition of the invention are well known to those of skill in the art. Such carriers include, for example, saline, buffered saline, liposomes, oil in water emulsions and others. The compositions may further include a detergent to make the peptide more bioavailable, e.g., octylglucoside. The present invention is not limited by the selection of the carrier or detergent.

Alternatively, the pharmaceutical compositions may be delivered as nucleotide sequences or may contain sequences which express the peptide or proteins of the invention in the host cell, which peptides are then secreted from the host cells. Suitable vehicles for direct DNA, plasmid nucleic acid, or recombinant vector administration include, without limitation, saline, sucrose, protamine, polybrene, polylysine, polycations, proteins, or spermidine, etc. [See e.g., International Patent Application No. WO94/01 139].

Pharmaceutical compositions of this invention may contain other active agents, such as conventional antibiotics, such as vancomycin [see, e.g., International Patent Application No. WO98/40401, published Mar. 10, 1998, incorporated by reference herein]. Alternatively, pharmaceutical compositions may be administered with other anti-pathogenic molecules or antibiotic compounds, such as conventional anti-fungals, e.g., itraconazole.

The pharmaceutical compositions may also be formulated to suit a selected route of administration, and may contain ingredients specific to the route of administration [see, e.g., Remington: The Science and Practice of Pharmacy, Vol. 2, 19$^{th}$ edition (1995)]. The preparation of these pharmaceutically acceptable compositions, from the above-described components, having appropriate pH isotonicity, stability and other conventional characteristics is within the skill of the art.

A method of treating a mammalian bacterial or fungal infection involves administering to an infected mammal an effective anti-bacterial or anti-fungal amount of a pharmaceutical composition described above. The method is useful in the treatment of infection caused by a Gram negative bacterium or Gram positive bacterium, such as those specifically identified in Example 2. The method may also be useful to treat fungal infections of the skin, nails, mucus membranes and intestines, e.g., candidiasis.

According to this invention, a pharmaceutical composition as described above may be administered by any appropriate route, but preferably by a route which transmits the peptide directly into the blood, e.g., intravenous injection. Other routes of administration include, without limitation, oral, intradermal, transdermal, intraperitoneal, intramuscular, intrathecal, subcutaneous, mucosal (e.g., intranasal), and by inhalation. If administered in the form of a nucleic acid preparation, e.g., wherein the sequence of the peptide is expressed in a recombinant viral vector or as naked DNA in a plasmid, the route is preferably intramuscular.

The amount of the protein, peptide or nucleic acid sequences of the invention present in each anti-bacterial effective dose is selected with regard to consideration of the pathogen causing the infection, the severity of infection, the patient's age, weight, sex, general physical condition and the like. The amount of active component required to induce an effective anti-bacterial or anti-fungal effect without significant adverse side effects varies depending upon the pharmaceutical composition employed and the optional presence of other components, e.g., antibiotics, anti-fungals and the like. Generally, for the compositions containing protein/peptide, or fusion protein, each dose will comprise between about 50 μg peptide/kg patient body weight to about 10 mg/kg. A more preferred dosage may be about 500 μg/kg of peptide. A more preferred dosage may be greater than 1 mg/kg or greater than 5 mg/kg. Other dosage ranges may also be contemplated by one of skill in the art. For example, dosages of the peptides of this invention may be similar to the dosages discussed for other peptide antibiotics, such as drosocin, although the peptides of this invention appear to be more potent than drosocin. See e.g., International Patent Application Nos. WO94/05787, WO99/05270, WO97/30082; and French patent Nos. 2733237, 2695392 and 2732345, among others. It has been noted for de-glycosylated pyrrhocoricin, that a dosage of about 50 mgs/kg body weight, enhances the infection. It has been surprisingly discovered that an anti-bacterial and/or anti-fungal effect results from administration of a dosage of deglycosylated pyrrhocoricin of less than 25 mgs/kg body weight, or preferably less than 10 mg/kg body weight.

Initial doses of the modified pyrrhocoricin of this invention may be optionally followed by repeated administration for a duration selected by the attending physician. Dosage frequency may also depend upon the factors identified above, and may range from 1 to 6 doses per day for a duration of about 3 days to a maximum of no more than about 1 week.

E. Use of the Peptides of this Invention in Drug Design, Screening and Development The peptides and polynucleotide sequences of the present invention may also be used in the screening and development of chemical compounds, small molecules or proteins which mimic the structure or activity of the peptides of this invention, and thus have utility as therapeutic drugs for the treatment of bacterial or fungal infections. These peptides may also be employed in assays to identify and isolate the stereospecific receptor located on the microorganisms against which the peptides are effective and with which they interact to achieve their anti-bacterial or anti-fungal effect. Identification of this receptor may also permit use of a variety of known techniques to design and develop other drugs having the anti-bacterial or antifungal effect of the peptides of this invention.

In one such embodiment, the peptides are employed in a suitable competitive assay method with test compounds to assess the ability of the test compound to competitively displace the peptide from binding to its presently unknown receptor on the pathogen. The steps of such a competitive assay may be readily determined by one of skill in the art. Where desired, and depending on the assay selected, a microorganism (e.g., bacterium or fungus) to which the selected peptide(s) are known to bind, e.g., *E. coli* strains, may be immobilized directly or indirectly on a suitable surface, e.g., in an ELISA format. Such immobilization surfaces are well known. For example, a wettable inert bead may be used. Further, the ligand may be bound to a 96 well plate. Thereafter selected amounts of the test compounds and the peptides of this invention are exposed to the immobilized microorganism and those test compounds selected which can compete with the peptides for binding to the immobilized microorganism. Once those test compounds which compete with the peptides for binding to the receptor on the bacteria or fungi are identified, they may be further screened for anti-bacterial or anti-fungal activities in the methods described in the examples below. It is within the skill of the art to prepare other conventional assay formats for identification of test compounds which compete with the peptides of this invention for binding to the unknown receptor.

Still another assay enables isolation of the receptor and thus the testing and identification of new peptides when the receptor is known. A selected peptide, such as the Biotin-K-pyrrhocoricin (Peptide 18) may be mixed with a French-pressed lysate of *E. coli* and the mixture incubated overnight. The mixture is centrifuged and the supernatant is loaded onto an agarose column to which an anti-biotin monoclonal antibody is conjugated. The column-bound receptor (and the attached biotin-K-pyrrhocoricin peptide) is eluted with a glycine buffer (pH 2.1). The full-sized receptor or its tryptic fragments are submitted to peptide sequencing and mass spectrometry. Alternatively the anti-biotin monoclonal antibody can be replaced with avidin or streptavidin. Yet another way is to couple other reporter groups to the pyrrhocoricin or Lys-pyrrhocoricin peptides, and isolate the receptor by using a monoclonal antibody or other specific binding partner to the reporter group.

Once the receptor is identified, it can be used to identify peptides other then pyrrhocoricin or its analogs that bind to that receptor. The following method may be used to verify the identity of the receptor. Preferably the peptides carry a fluorescing or fluoresceinating reporter group, such as fluorescein-Lys-pyrrhocoricin (Peptide 19). A 2 nM solution of fluorescein-labeled test peptide is mixed with a PBS solution of the receptor in which the concentration of the receptor varies from 1 nM to 100 μM. The binding curve is measured by fluorescence polarimetry.

The identity of the receptor is not essential to the performance of such assays. Identification of useful anti-bacterial/anti-fungal test compounds permit the screening and development of identification, e.g., the screening of combinatorial libraries, of non-peptide antibiotics which mimic the activity of a peptide of this invention.

Other assays and techniques also exist for the identification and development of compounds and drugs which mimic the structure or activity of a peptide of this invention. These include the use of phage display system for expressing the peptide(s), and the use of a culture of transfected *E. coli* or other microorganism to produce the peptides for binding studies of potential binding compounds. See, for example, the techniques described in G. Cesarini, *FEBS Letters*, 307(1):66–70 (July 1992); H. Gram et al, *J. Immunol. Meth.*, 161:169–176 (1993); C. Summer et al, *Proc. Natl. Acad. Sci., USA*, 89:3756–3760 (May 1992), incorporated by reference herein.

Other conventional drug screening techniques may be employed using the peptides and polynucleotide sequences of this invention. As one example, a method for identifying compounds which specifically bind to a peptide of this invention can include simply the steps of contacting a selected peptide with a test compound to permit binding of the test compound to the peptide; and determining the amount of test compound, if any, which is bound to the peptide. Such a method may involve the incubation of the test compound and the anti-bacterial-anti-fungal peptide immobilized on a solid support.

Typically, the surface containing the immobilized ligand is permitted to come into contact with a solution containing the peptide and binding is measured using an appropriate detection system. Suitable detection systems include the streptavidin horse radish peroxidase conjugate, direct conjugation by a tag, e.g., fluorescein. Other systems are well known to those of skill in the art. This invention is not limited by the detection system used.

Another method of identifying compounds which specifically bind to the peptides of this invention can include the steps of contacting the peptide, immobilized on a solid support with both a test compound and a proposed receptor for the peptide to permit binding of the receptor to the peptide; and determining the amount of the receptor which is bound to the peptide.

The peptides of the present invention are also useful in assays to identify the stereospecific receptor with which these peptides interact to produce their anti-bacterial effect. Such assays and the identification of the receptor enable additional screening of further pathogens against which the peptides or test compounds as identified above are effective peptides and/or pharmaceutical compounds that bind the same receptor and have an antibiotic effect.

A compound which has structural similarity to the peptide, or the binding portion of the peptide to the receptor may also be computationally evaluated and designed by means of a series of steps in which chemical entities or fragments are screened and selected for their ability to associate with the peptides of this invention. One skilled in the art may use one of several methods to screen chemical entities or fragments for their ability to mimic the structure of these peptides and more particularly to identify the peptide structure that binds with the stereospecific receptor of pyrrhocoricin. This process may begin by visual inspection of, for example, a three dimensional structure of the peptides of this invention on the computer screen. Selected fragments or chemical entities may then be positioned in a variety of orientations to determining structural similarities, or docked, within a putative binding site of the peptide.

Specialized computer programs that may also assist in the process of selecting fragments or chemical entities similar to the peptides, or entities which can interact with the peptides and thus mimic the receptor, include the GRID program available from Oxford University, Oxford, UK. [P. J. Goodford, "A Computational Procedure for Determining Energetically Favorable Binding Sites on Biologically Important Macromolecules", *J. Med. Chem.*, 28:849–857 (1985)]; the MCSS program available from Molecular Simulations, Burlington, Mass. [A. Miranker and M. Karplus, "*Functionality Maps of Binding Sites: A Multiple Copy Simultaneous Search Method*", Proteins: Structure, Function and Genetics, 11:29–34 (1991)]; the AUTODOCK program available from Scripps Research Institute, La Jolla, Calif. [D. S. Goodsell and A. J. Olsen, "*Automated Docking of Substrates to Proteins by Simulated Annealing*", Proteins: Structure, Function, and Genetics, 8:195–202 (1990)]; and the DOCK program available from University of California, San Francisco, Calif. [I. D. Kuntz et al, "*A Geometric Approach to Macromolecule-Ligand Interactions*", *J. Mol. Biol.*, 161: 269–288 (1982)], and software such as Quanta and Sybyl, followed by energy minimization and molecular dynamics with standard molecular mechanics force fields, such as CHARMM and AMBER. Additional commercially available computer databases for small molecular compounds include Cambridge Structural Database, Fine Chemical Database, and CONCORD database [for a review see Rusinko, A., *Chem. Des. Auto. News*, 8:44–47 (1993)].

Once suitable chemical entities or fragments have been selected, they can be assembled into a single compound or inhibitor. Assembly may proceed by visual inspection of the relationship of the fragments to each other on the three-dimensional image displayed on a computer screen in relation to the structure of the peptide. Useful programs to aid one of skill in the art in connecting the individual chemical entities or fragments include the CAVEAT program [P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc. 78, pp. 182–196 (1989)], which is available from the University of California, Berkeley, Calif.; 3D Database systems such as MACCS-3D database (MDL Information Systems, San Leandro, Calif.) [see, e.g., Y. C. Martin, "3D Database Searching in Drug Design", *J. Med. Chem.*, 35:2145–2154 (1992)]; and the HOOK program, available from Molecular Simulations, Burlington, Mass.

Compounds that mimic a peptide of this invention may be designed as a whole or "de novo" using methods such as the LUDI program [H. -J. Bohm, "The Computer Program LUDI: A New Method for the De Novo Design of Enzyme Inhibitors", *J. Comp. Aid. Molec. Design*, 6:61–78 (1992)], available from Biosym Technologies, San Diego, Calif.; the LEGEND program [Y. Nishibata and A. Itai, *Tetrahedron*, 47:8985 (1991)], available from Molecular Simulations, Burlington, Mass.; and the LeapFrog program, available from Tripos Associates, St. Louis, Mo. Other molecular modeling techniques may also be employed in accordance with this invention. See, e.g., N. C. Cohen et al, "Molecular Modeling Software and Methods for Medicinal Chemistry", *J. Med. Chem.*, 33:883–894 (1990). See also, M. A. Navia and M. A. Murcko, "The Use of Structural Information in Drug Design", *Current Opinions in Structural Biology*, 2:202–210 (1992). For example, where the structures of test compounds are known, a model of the test compound may be superimposed over the model of the peptide of the invention. Numerous methods and techniques are known in the art for performing this step, any of which may be used. See, e.g., P. S. Farmer, *Drug Design*, Ariens, E. J., ed., Vol. 10, pp 119–143 (Academic Press, New York, 1980); U.S. Pat. No. 5,331,573; U.S. Pat. No. 5,500,807; C. Verlinde, *Structure*, 2:577–587 (1994); and I. D. Kuntz, Science, 257:1078–1082 (1992). The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual synthesis of many compounds is effectively eliminated.

Once identified by the modeling techniques, the proposed "new antibacterial or anti-fungal" compound may be tested for bioactivity using standard techniques, such as the in vitro assay of Example 2 below. Suitable assays for use herein include, but are not limited to, the assays shown below in the examples to detect the anti-bacterial effect of the peptides of this invention. However, other assay formats may be used and the assay formats are not a limitation on the present invention.

The following examples illustrate various aspects of this invention. These examples do not limit the scope of this invention which is defined by the appended claims.

EXAMPLE 1

Production of Peptides of this Invention

Modified pyrrhocoricin peptides were designed by conventional peptide synthesis techniques. Peptides were assembled on solid-phase using a Milligen 9050 continuous flow automated peptide synthesizer on a Fmoc-PAL-polyethylene glycolpolystyrene copolymer resin with an initial load of 0.17 mmole/g (PerSeptive Biosystems, Warrington, UK) using standard Fmoc chemistry [G. B. Fields et al, *Int. J. Pept. Protein Res.,* 35:161–124 (1990)]. A 4-molar excess of the acylating amino acids and 1-hydroxy-7-azabenzotriazole uronium salt (HATU) activation were used, as recommended for the synthesis of complex peptides [Y. Angell et al, *Tetrahedron Lett.,* 35:5891:5894 (1994)]. The side chain protecting groups were trityl for Asn, tert-butyl ether for Tyr, Ser and Thr, tert-butyl ester for Asp, 2,2,5,7,8-pentamethylchroman-6-sulfonyl for Arg, and tert-butyloxy-carbonyl for Lys. A glycosylated Asn residue was incorporated in the same manner as unmodified amino acids. Fmoc diaminopropionic acid (Bachem Biosciences) was acetylated with equimolar amounts of pentafluorophenyl acetate prior to peptide synthesis and was used for peptide assembly without any further purification. The glycopeptides were synthesized from commercially available glycoaminoacid building blocks, including Fmoc-Thr [Gal(Ac$_4$)GalNAc(Ac$_2$)]-OH and Fmoc-Asn[GlcNAc(Ac$_3$)]-OH (Novabiochem, San Diego, Calif.). Peptides were cleaved from the solid support by TFA in the presence of m-cresol (5%), ethane-dithiol (2.5%), thioanisole (5%), and water (5%) as scavengers for 2–3 hours. Deacetylation of the sugar hydroxyl groups was accomplished by a 2 minute treatment with 0.1 M NaOH. After cleavage, peptides were purified by reversed phase high performance liquid chromatography (RP-HPLC). The final products were characterized by amino acid analysis and matrix assisted laser desorption/ionization (MALDI-MS) by standard methods. Mass spectra verified the anticipated composition of the peptides.

The modifications of the unmodified pyrrhocoricin according to this invention include—terminal and C-terminal modifications to protect the peptide from exopeptidase cleavage. Two endopeptidase cleavage sites were identified, i.e., between Ser5 and Tyr6 and between Asn18 and Arg19. Other modifications include providing a positive charge at, or near, the native amino terminus, and inserting unnatural, glycosylated or D-amino acid residues to the—and C-termini to improve stability in serum. Still other modifications to the pyrrhocoricin are cyclizing the peptide to prevent cleavage by exopeptidases. Replacing conventional amide bonds between one or more amino acids in the sequence with bonds less sensitive to cleavage by proteases, e.g., thioamide bonds or reduced amide bonds, is also a desirable modification. Such a modification of bonds can desirably occur between Ser5 and Tyr 6 or between Asn18 and Arg19, or at both sites. Still other sites in the sequence may be so modified.

The native unmodified pyrrhocoricin contains on the 11$^{th}$ amino acid residue Thr of pyrrhocoricin, the sugar, galactose (Gal)-2-acetamido-2-deoxy-galactose (GalNAc), as follows:

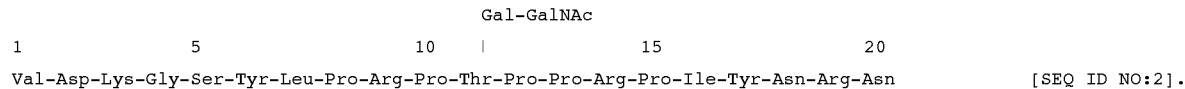

```
                                    Gal-GalNAc
1              5              10       |        15                  20
Val-Asp-Lys-Gly-Ser-Tyr-Leu-Pro-Arg-Pro-Thr-Pro-Pro-Arg-Pro-Ile-Tyr-Asn-Arg-Asn       [SEQ ID NO:2].
```

For use in the following assays, native pyrrhocoricin is referred to as Peptide 2.

The modifications of the de-glycosylated (non-native) pyrrhocoricin amino acid sequences which provide peptides of this invention as well as control (inactive) peptides, appear in the sequences below in bolded, italicized print for ease of review. These peptides are identified by the following peptide numbers throughout the examples. In the modified peptides 1, and 3–25 below, all amino acids were of the L-configuration, except for peptides 12 and 13, in which the indicated amino acids were of the D-configuration. All carbohydrates were of the D-configuration. The following peptides are modified versions of pyrrhocoricin, of which Peptides 1, 3–6,8–12, and 17–24 are novel anti-bacterial peptides of this invention; and Peptides 7, 13–16 and 25 are modified inactive peptides shown for comparative purposes.

Active, modified Peptide 1 is a pyrrhocoricin which is deleted in the naturally occurring mid-chain glycosylation, but which has the following 20 amino acid sequence:

Val-Asp-Lys-Gly-Ser-Tyr-Leu-Pro-Arg-Pro-Thr-Pro-Pro-Arg-Pro-Ile-Tyr-Asn-ArgAsn [SEQ ID NO: 6].

Active, modified Peptide 3 has the sequence:

Acetyl-Lys-Val-Asp-Lys-Val-Asp-Lys-Gly-Ser-Tyr-Leu-Pro-Arg-Pro-Thr-Pro-ProArg-Pro-Ile-Tyr-Asn-Arg-Asn [SEQ ID NO: 7].

Active, modified Peptide 4 has the sequence:

Acetyl-Arg-Val-Asp-Lys-Gly-Ser-Tyr-Leu-Pro-Arg-Pro-Thr-Pro-Pro-Arg-Pro-IleTyr-Asn-Arg-Asn [SEQ ID NO: 8].

Active, modified Peptide 5 has the sequence:

Acetyl-Lys-Val-Asp-Lys-Gly-Ser-Tyr-Leu-Pro-Arg-Pro-Thr-Pro-Pro-Arg-Pro-IleTyr-Asn-Arg-Asn [SEQ ID NO: 9].

In the active, modified Peptide 6, the R$^1$ moiety is 1-aminocyclo-hexane carboxylic acid. The sequence is

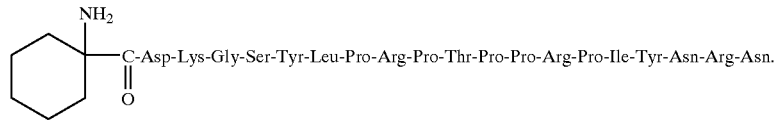

[SEQ ID NO:10]

Inactive Peptide 7 is acetylated on its N-terminus and retains the galactose-2-acetamido-2-deoxy-galactose (Gal-GalNAc) modifying the 11$^{th}$ amino acid of native pyrrhocoricin. The sequence is:

[SEQ ID NO:11]

Active, modified Peptide 8 has the positively charged N-terminal acetyl-lysine group, and a C-terminal imide group which cyclizes the 20$^{th}$ amino acid residue and has the sequence [SEQ ID NO: 12]:

Active, modified Peptide 9 has a positively charged N-terminal acetyl-Lysine and a β-acetyl-2,3-diamino propionic amide group (DapAc) in the L configuration attached to the 19$^{th}$ amino acid residue with the 20$^{th}$ amino acid residue eliminated. The sequence is:

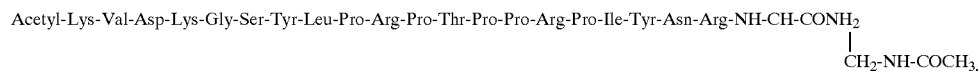

[SEQ ID NO:13]

Active, modified Peptide 10 has a positively charged N-terminal acetyl-Lysine and a 2-acetamido-2-deoxyglucose (GlcNAc) group modifying the 20$^{th}$ amino acid residue on the C-terminus. The sequence is:

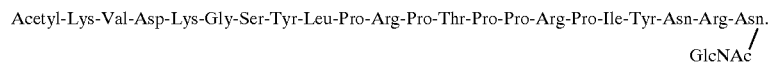

[SEQ ID NO:14]

Active, modified Peptide 11 has an N-terminal acetyl-Lysine and a triacetyl-2-acetamido-2-deoxyglucose (Ac3-GlcNAc) group modifying the 20th amino acid residue on the C-terminus. The sequence is:

[SEQ ID NO:15]

Acetyl-Lys-Val-Asp-Lys-Gly-Ser-Tyr-Leu-Pro-Arg-Pro-Thr-Pro-Pro-Arg-Pro-Ile-Tyr-Asn-Arg-Asn.
/
Ac3-GlcNAc Peptide 12 is a somewhat active modified peptide having the first amino acid residue Val in the D configuration, and the 20 amino acid Asn in the D configuration, with the sequence:
D-Val-Asp-Lys-Gly-Ser-Tyr-Leu-Pro-Arg-Pro-Thr-Pro-Pro-Arg-Pro-Ile-Tyr-AsnArg-D-Asn [SEQ ID NO:16].

Inactive Peptide 13 is a pyrrhocoricin without the mid-chain glycosylation and with all amino acid residues in the D configuration:
Val-Asp-Lys-Gly-Ser-Tyr-Leu-Pro-Arg-Pro-Thr-Pro-Pro-Arg-Pro-Ile-Tyr-Asn-ArgAsn [SEQ ID NO:26].

Inactive Peptides 14 and 15 are 9 and 11 amino acid fragments, respectively, of pyrrhocoricin, having the sequences:
Val-Asp-Lys-Gly-Ser-Tyr-Leu-Pro-Arg [amino acids 1–9 of SEQ ID NO: 6] and Pro-Thr-Pro-Pro-Arg-Pro-Ile-Tyr-Asn-Arg-Asn [amino acids 10–20 of SEQ ID NO: 6, deleted of glycosylation].

Inactive Peptide 16 is a cyclic peptide in which the spacer is an additional Lys-Val dipeptide residue joining the N-terminal amino acid to the negatively charged (precyclization) C-terminal amino acid. This spacer restricts the structure of the peptide. This peptide has the sequence as follows:

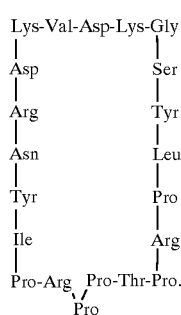

[SEQ ID NO:17]

The most active of the peptides of this invention is modified Peptide 17, which is a cyclic non-glycosylated peptide. In this peptide, a lysine residue was added to the amino terminus of the peptide, which is cyclized with an 8 residue spacer between the original N- and C-termini. The spacer corresponds to the middle domain (amino acid residues 7–14) of pyrrhocoricin and is incorporated backwards to remain in register with the original copy of this fragment. This arrangement retained with native orientation of the bioactive domains, i.e., the original termini. This peptide has the sequence as follows:

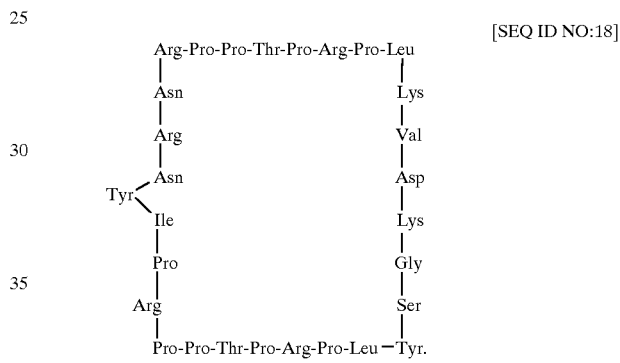

[SEQ ID NO:18]

Active, modified Peptide 18 has a positively charged biotin-Lys-Val group attached at the N-terminus, and having the sequence:
Biotin-Lys-Val-Asp-Lys-Gly-Ser-Tyr-Leu-Pro-Arg-Pro-Thr-Pro-Pro-Arg-Pro-Ile5 Tyr-Asn-Arg-Asn-[SEQ ID NO:19].

Active modified Peptide 19 has a positively charged group with a reporter sequence attached at the N-terminus, and having the sequence:
5(6)-carboxyfluorescein-Lys-Val-Asp-Lys-Gly-Ser-Tyr-Leu-Pro-Arg-Pro-Thr-ProPro-Arg-Pro-Ile-Tyr-Asn-Arg-Asn-[SEQ ID NO:20].

Weakly active, modified Peptide 20 has the positively charged Acetyl-Lys-Val attached at the N-terminus, and replaces the C-terminal Asparagine with Aspartic acid. The sequence is:
Acetyl-Lys-Val-Asp-Lys-Gly-Ser-Tyr-Leu-Pro-Arg-Pro-Thr-Pro-Pro-Arg-Pro-IeTyr-Asn-Arg-Asp- SEQ ID NO:21].

Active, modified Peptide 21 has an $R^1$ group of 1-aminocyclo-hexane carboxylic acid, and having attached at the C-terminus in place of the 19th amino acid Asn, a β-acetyl-2,3-diamino propionic amide group in the L configuration.

The sequence is:

[SEQ ID NO:22]

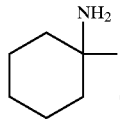

The active, modified Peptide 22 has an Acetyl-Arg group attached to the N-terminal Val, and having attached at the C-terminus in place of the 20th amino acid Asn, a β-acetyl-2,3-diamino propionic amide group in the L configuration. The sequence is:

[SEQ ID NO:23]

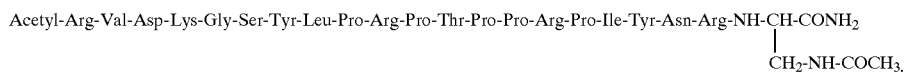

Inactive Peptide 23 has the $R^1$ group 1-aminocyclohexane carboxylic acid, and replaces Ser5 and Tyr6 with Ala5 and Phe6. Attached at the C-terminus in place of the 19th amino acid Asn is a β-acetyl-2,3-diamino propionic amide group in the L configuration. The sequence is [SEQ ID NO:24]:

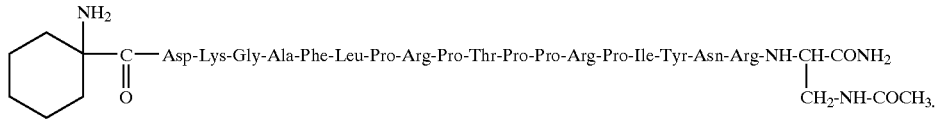

Active Peptide 24 has attached at the C-terminus in place of the 20th amino acid Asn, a β-acetyl-2,3-diamino propionic amide group in the L configuration:

[SEQ ID NO:25]

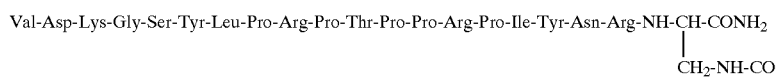

Inactive Peptide 25 is a fragment of pyrrhocoricin having the sequence:
Val-Asp-Lys-Gly-Ser-Tyr-Leu-Pro-Arg-Pro-Thr-Pro-Pro-Arg-Pro-Ile-Tyr-Asn [amino acids 1–18 of SEQ ID NO: 6].

These peptides are tested in some or all of the following assays of Examples 2–4 below.

EXAMPLE 2

In Vitro Anti-Bacterial Activity of the Peptides

Growth inhibition assays were performed using the peptides of Example 1 and the Gram positive microorganisms *Micrococcus luteus* and *Bacillus megaterium*, and the Gram negative microorganisms, *Escherichia coli* D22, *Agrobacterium tumefaciens*, and *Salmonella typhimurium*. Anti-bacterial assays were performed in sterilized 96-well plates (Nunc F96 microtiter plates) with a final volume of 100 μl as described in Bulet (1996), cited above. Briefly, 90 μl of a suspension of a midlogarithmic phase bacterial culture at an initial 600 nm UV absorbence of 0.001 in Luria-Bertani rich nutrient medium was added to 10 μl of serially diluted peptides in sterilized water. The final peptide concentrations ranged between 0.15 and 80 μM. The plates were incubated at 30° C. for 24 hours with gentle shaking, and the growth inhibition was measured by recording the increase of the UV absorbence at 600 nm on an SLT Labinstruments 400 ATC microplate reader. The experiments were conducted over a 7-month period.

Table 1 reports the inhibitory concentrations ($IC_{50}$) of each peptide #1 to #25 [SEQ ID NOS: 2 and 6–26] identified in Example 1 against each above-indicated microorganism. $IC_{50}$ is defined as the concentration in μM at which 50% growth inhibition of the indicated microorganism is observed. To assess the variability of the assay, Peptide 22 [SEQ ID NO: 23] was reassayed after 3 months of the original date, and both the original (a) and 3 month (b) results are reported in the table. No activity up to 80 μM concentration is indicated by "-"; an $IC_{50}$ greater than 10 is essentially evidence of an inactive peptide.

TABLE I

| # | Micro-coccus luteus | Bacillus megaterium | Escherichia coli D22 | Agrobacterium tumefaciens | Salmonella typhimurium |
|---|---|---|---|---|---|
| | | | IC$_{50}$ in $\mu$M against | | |
| 1 | 10 | 5 | <0.075 | <0.075 | 0.6 |
| 2 | — | 40 | 0.3 | 0.3 | 2.5 |
| 3 | 80 | — | 0.3 | 10 | 5 |
| 4 | 5 | — | 0.6 | 2.5 | 2.5 |
| 5 | 40 | — | 0.6 | 5 | 40 |
| 6 | 5 | 10 | 0.3 | 1.25 | 2.5 |
| 7 | — | — | 10 | — | — |
| 8 | 5 | 20 | 0.3 | 1.25 | 2.5 |
| 9 | 10 | 40 | 0.6 | 1.25 | 1.25 |
| 10 | 40 | — | 0.6 | 5 | 2.5 |
| 11 | 40 | 40 | 0.6 | 2.5 | 20 |
| 12 | 10 | — | 0.6 | 2.5 | 5 |
| 13 | 40 | — | — | — | — |
| 14 | — | — | — | — | — |
| 15 | — | — | — | — | — |
| 16 | — | — | — | — | — |
| 17 | 0.6 | 2.5 | 0.6 | 2.5 | 5 |
| 18 | 5 | — | <0.15 | 1.25 | 1.25 |
| 19 | 80 | — | 5 | 20 | 40 |
| 20 | — | — | 2.5 | 40 | — |
| 21 | 10 | 40 | 0.6 | 5 | 2.5 |
| 22 a/b | 10/10 | 40/80 | 0.3/0.3 | 2.5/0.6 | 2.5/2.5 |
| 23 | 5 | 40 | 20 | — | — |
| 24 | 5 | 20 | <0.3 | <0.3 | <0.3 |
| 25 | — | — | — | — | — |

The two putative binding sites cannot be separated (see, Peptides 14 and 15) [aa 1–9 and aa 10–20, respectively of SEQ ID NO: 6]. An equimolar mixture of shorter Peptides 14 and 15 remained inactive in all five bacterial strains studied. An analog made of only D-amino acids was similarly inactive (Peptide 13) [SEQ ID NO: 26], indicating that pyrrhocoricin binds stereospecifically to a target protein. The N-terminus of the native glycopeptide (Peptide 7) [SEQ ID NO: 11] could not be blocked without a major loss of anti-bacterial activity. Pyrrhocoricin analogs containing labels and an additional lysine at the N-terminus (Peptides 18 and 19) [SEQ ID NOS: 19 and 20] retain biological activity.

The results in Table 1 demonstrate several additional characteristics of the modified peptides of this invention vs. the unmodified Peptides 1 and 2 [SEQ ID NO: 6 and 2, respectively]. The differences in the IC$_{50}$ values between the results for Peptide 22 [SEQ ID NO: 23] in two performances of the assay (at time a and 3 months later at time b) demonstrate the variability of the assays. In general, modifications at either termini reduced the potency of unmodified pyrrhocoricin. From the N- or C-terminally modified peptides, the modifications of a 1-aminocyclo-hexane carboxylic acid at the amino terminus and a β-acetyl-2,3-diamino propionic amide group at the carboxy-terminus retained most of the anti-bacterial activity. In a preferred embodiment for drug development, both termini are modified to block or at least retard exopeptidase cleavage. Peptides containing modifications at both termini featured acetylation together with positively charged amino acid addition, incorporation of unnatural amino acids, such as Chex or Dap(Ac), glycosylation, imide formation, D-amino acid substitution or cyclization. Examples of desirable peptides having modifications at both termini are Peptides # 8, 9, 10, 11, 12, 13, 16, 17, 21, and 22 [SEQ ID NOS: 12–16, 26, 17, 18, 22 and 23, respectively].

Considering the time of the assay and the requirement for submicromolar activity against at least one strain, Peptide 1 [SEQ ID NO: 6], Peptide 17 [SEQ ID NO: 18], Peptide 21 [SEQ ID NO: 22] and Peptide 22 [SEQ ID NO: 23], described above in Example 1 were selected for further studies, which include normal cell toxicity and serum stability assays followed by in vivo efficacy studies. These peptides show remarkable activity against Gram negative bacteria. The best analog for killing Gram-negative and Gram-positive bacteria (e.g., wide spectrum activity) is cyclic Peptide 17, which demonstrated a broad activity spectrum at low micromolar concentrations.

EXAMPLE 3

Assays for Toxicity to Mammalian Cells

A. Hemolytic Activity

To determine whether native and modified pyrrhocoricin peptides were toxic to mammalian cells, several peptides from Example 1 above, a positive control, and a negative control were examined for hemolytic activity. Hemolytic activity was assayed with sheep erythrocytes suspended in Alsever's solution (BioWhittaker, Walkersville, Md.), and diluted with Dulbecco's phosphate-buffered saline, pH 7.2. Thirty $\mu$L of a 1% suspension of the red blood cells was incubated with agitation at 39° C. with 30 $\mu$L of 40 to 256 $\mu$M of each of the following peptides dissolved in phosphate buffered saline for one hour and centrifuged at 1000 g for five minutes. Fifty $\mu$L of the supernatant was collected and the release of hemoglobin was detected by measuring the ultraviolet absorbences of triplicate samples of the 40 $\mu$M or 256 $\mu$M test peptides and the control peptides at 405 nm.

The peptides tested in this assay were Peptide 1, Peptide 21, Peptide 22, and Peptide 23 [SEQ ID NOS: 6, 22, 23 and 24, respectively] from Example 1. The positive control was melittin, which has the sequence:
Gly-Ile-Gly-Ala-Val-Leu-Lys-Val-Leu-Thr-Thr-Gly-Leu-Pro-Ala-Leu-Ile-Ser-Trp-eLys-Arg-Lys-Arg-Gln-Gln-amide (Bachem, King of Prussia, Pa.) [SEQ ID NO:27]. The negative control was peptide 31D, a T helper cell epitope [Ertl et al, *J. Virol.*, 63:2885–2892 (1989)] having the sequence: Ala-Val-Tyr-Thr-Arg-Ile-Met-Met-Asn-Gly-Gly-Arg-Leu-Lys-Arg-amide [SEQ ID NO:28]. The results of this assay are reported below in Table 2.

TABLE 2

| Peptide # | Absorbence at 405 nm | |
|---|---|---|
| | 40 $\mu$M | 256 $\mu$M |
| 1 | 0.108 ± 0.015 | 0.0135 ± 0.005 |
| 21 | 0.110 ± 0.049 | 0.143 ± 0.006 |
| 22 | 0.126 ± 0.019 | — |
| 23 | 0.118 ± 0.035 | — |
| Melittin (positive control) | 2.99 ± 0.06 | — |
| 31D (negative control) | 0.160 ± 0.021 | — |

At a final concentration of 40 $\mu$M, only melittin lysed the erythrocytes. The lowest concentration in which melittin lysed sheep erythrocytes was 5 $\mu$M, in agreement with the findings of Wade et al, *Proc. Natl. Acad. Sci. USA*, 87:4761–4765 (1990). When the pyrrhocoricin and the modified Chex-pyrrhocoricin-Dap(Ac) peptide were increased to 256 $\mu$M concentration, the peptides remained completely non-toxic to sheep erythrocytes.

B. Direct Killing of Immortalized COS Cells

In another toxicity assay, COS cell survival was studied for pyrrhocoricin and cecropin B (Bachem Biosciences, King of Prussia, Pa.) as the positive control. Cecropin B was used as a positive control because this channel-forming anti-bacterial peptide was shown to kill a wide range of immortalized tumor cells [A. J. Moore et al, *Peptide Res.*, 5:265–269 (1994)]. The results are indicated in Table 3.

TABLE 3

| Peptide | Cell Count after Treatment |
| --- | --- |
| No peptide | 13.5 ± 9.5 |
| 5 μM Cecropin | 6 ± 6 |
| 10 μM Cecropin | 6.7 ± 0.3 |
| 50 μM Cecropin | 7.3 ± 3.7 |
| 5 μM Pyrrhocoricin | 18 ± 4 |
| 10 μM Pyrrhocoricin | 12 ± 4 |
| 50 μM Pyrrhocoricin | 11 ± 1 |

While cecropin reduced the cell count at as low as 5 μM concentration, the cell count and rate of proliferation did not change after addition of up to 50 μM/mL concentration of pyrrhocoricin.

EXAMPLE 4

Peptide Stability 1N Serum

In vivo stability of peptides in blood is currently modeled well by in vitro stability in serum or plasma (neglecting renal and hepatic clearance). Serum stability studies represent one of the most important secondary screening assays in peptide drug development, largely because they eliminate peptides that have short half-lives and are therefore unlikely to be therapeutically effective. Owing to the fact that the use of diluted serum increases peptide recovery as well as retards the reaction kinetics to a manageable rate, the experiments were conducted using 25% aqueous sera. It was earlier demonstrated that the degradation rates are linearly proportional to serum concentration [M. F. Powell et al, *J. Pharm. Sci.*, 81: 731–735 (1992)].

For serum stability studies, 10 μl of an aqueous peptide stock solution containing about 0.8 mg/ml peptide was added to 200 μl 25% aqueous pooled mouse or human serum (Sigma, St. Louis, Mo.), according to the process described in M. F. Powell et al, *Pharmacol Res*, 10: 1268–1273 (1993). The peptide-serum mixture was thermostated at 37° C. After 0 minutes, 45 minutes, 2 hours and 4 hours, three samples of each peptide were taken and precipitated by the addition of 40 μl 15% aqueous trichloroacetic acid. The samples were stored at 4° C. for 20 minutes and centrifuged. The peptides and some remaining serum proteins were recovered in the supernatant after the trichloroacetic acid precipitation. The supernatants were immediately frozen on dry-ice and 220 μl of each were analyzed on RP-HPLC. A mouse serum and two different batches of the same SIGMA catalog number of human sera (human 1, approximately 1 year old, and human 2, approximately 1 month old) were also used.

To obtain comparable data, all peptide degradation at 0 minutes is adjusted to 100%. The lyophilized samples were redissolved in 0.1 aqueous TFA and submitted for matrix assisted laser desorption/ionization (MALDI-MS).

The degradation products of the modified peptides of this invention (Peptides 1, 21 and 22 [SEQ ID NOS: 6, 22 and 23, respectively]) after a 45-minute digestion with 25% mammalian sera are reported in Table 4. The missing residues are indicated (e.g—C2 means that the C-terminal two residues are cleaved off). For Peptide 22 (which is a modified pyrrhocoricin, having an acetyl-Arg group attached to the N-terminal Val, and having attached at the C-terminus in place of the 20$^{th}$ amino acid Asn, a β-acetyl-2,3-diamino propionic amide group in the L configuration), the N-terminal residue numbers correspond to unmodified pyrrhocoricin. In Table 4, the relative amounts of the degradation products are estimated based on the MALDI-MS peak heights. 0=not detected; 1=very weak (below 5000), 2=weak (5–10000), 3=medium (10–15000), 4=strong (15000-uncleaved molecular ion at 25–30000), 5=very strong (above uncleaved molecular ion). All identified degradation products are listed.

TABLE 4

| Peptide # | Serum | Degradation Products | | | | | | | |
| --- | --- | --- | --- | --- | --- | --- | --- | --- | --- |
| | | -C1 | -C2 | -C3 | -C6 | -N3 | -N5 | -N3, C2 | -N5, C2 |
| 1 | mouse | 2 | 2 | 0 | 0 | 0 | 0 | 0 | 0 |
| | human 1 | 3 | 4 | 3 | 1 | 0 | 2 | 0 | 0 |
| | human 2 | 2 | 2 | 0 | 0 | 0 | 0 | 0 | 0 |
| 21 | mouse | 0 | 2 | 0 | 0 | 0 | 2 | 0 | 0 |
| | human 1 | 0 | 4 | 2 | 0 | 0 | 2 | 0 | 1 |
| | human 2 | 0 | 4 | 0 | 0 | 0 | 2 | 0 | 1 |
| 22 | mouse | 0 | 2 | 0 | 0 | 0 | 0 | 0 | 0 |
| | human 1 | 0 | 5 | 3 | 0 | 2 | 3 | 1 | 2 |
| | human 2 | 0 | 5 | 0 | 0 | 2 | 1 | 0 | 0 |

When looking at the first metabolites after 45 minute digestion, it is evident that the C-terminal asparagine is cleaved off Peptide 1 [SEQ ID NO: 6]. In contrast, the modified C-terminal residue stays on the peptides containing β-acetyl-2,3-diamino propionic amide residues (Peptides 21 and 22) [SEQ ID NOS: 22 and 23, respectively]. The acetyl-Arg amino terminal modified Peptide 22 produces more N-terminal cleavage products close to the amino terminus than Peptide 21 (which is a modified pyrrhocoricin, having in place of the N-terminal Val, the group 1-aminocyclo-hexane carboxylic acid-, and having attached at the C-terminus in place of the 20$^{th}$ amino acid Asn, a β-acetyl-2,3-diamino propionic amide group in the L configuration). Most notably, Peptide 21 produces a fragment in which the Val-Asp-Lys tripeptide is missing. While for Peptide 1 the degradation products are different in the two human sera, for Peptide 21, they are very similar. They are also similar to those observed after digestion with the mouse serum. Apparently, Peptide 21, is generally more resistant than Peptide 1 in human serum.

FIG. 1 shows the kinetics of the degradation of Peptides 1 and 21 [SEQ ID NOS: 6 and 22, respectively] in this assay. The curves are fitted to an exponential equation. The degradation curves for Peptide 1 and Peptide 21 (the modified pyrrhocoricin, having in place of the N-terminal Val, the group 1-aminocyclo-hexane carboxylic acid-, and having attached at the C-terminus in place of the 20$^{th}$ amino acid Asn, a β-acetyl-2,3-diamino propionic amide group in the L configuration) were similar. Nonglycosylated pyrrhocoricin is somewhat more stable in mouse serum and in the weaker human serum, but much less stable in the more active human serum. Although the lack of endopeptidase cleavage sites reduced the degradation rate of Peptide 21 compared to Peptide 1, this loss of protease activity was compensated for increased exopeptidase activity C-terminal to Ser5 and Asn18. Preliminary metabolism studies of the cyclic Peptide 17 [SEQ ID NO: 18] indicated an endopeptidase cleavage site between Asn 18 and Arg19 in human sera. In accordance with the increased number and amount of N-terminal degradation products, Peptide 22 [SEQ ID NO: 23](a modified pyrrhocoricin, having an acetyl-Arg group attached to the N-terminal Val, and having attached at the C-terminus in place of the $20^{th}$ amino acid Asn, a β-acetyl-2,3-diamino propionic amide group in the L configuration), degrades considerably faster than either Peptide 1 or Peptide 21 (not shown). Remarkably, after 8 hours of digestion, in mouse serum, both Peptides 1 and 21 have 20% of the initial amounts intact. Significantly, after the same period of time, traces of Peptide 21 are still present in all sera studied.

EXAMPLE 5

In Vivo Anti-bacterial Activity of the Peptides

Peptides 1, 17 and 21 [SEQ ID NOS: 6, 18, and 22, respectively] are comparatively evaluated in an in vivo anti-bacterial assay performed as follows: Male mice of CD-1 strain (Harlan Sprague Dawley, Inc.) were intravenously infected in the tail with 1,000,000 colony forming units (0.2 ml) of *Escherichia coli* strain (ATCC Accession No. 25922). To obtain better infection, mice are also fed with *E. coli*. The test peptides are intravenously injected 1 hour after infection at doses of 10, 25 and 50 mg/kg, followed by a booster injection after 5 hours of infection. Mice were observed at 1 hour, 5 hours, 1 day, and 2 days post-infection for clinical signs (e.g., decreased activity and head tilt) or mortality, and were compared with control mice who received 5% dextrose (DS5) instead of peptides (negative control) or were submitted to the same peptide treatment, but received 50 mg/kg of DS5 instead of the bacteria (toxicity).

Figure 2:
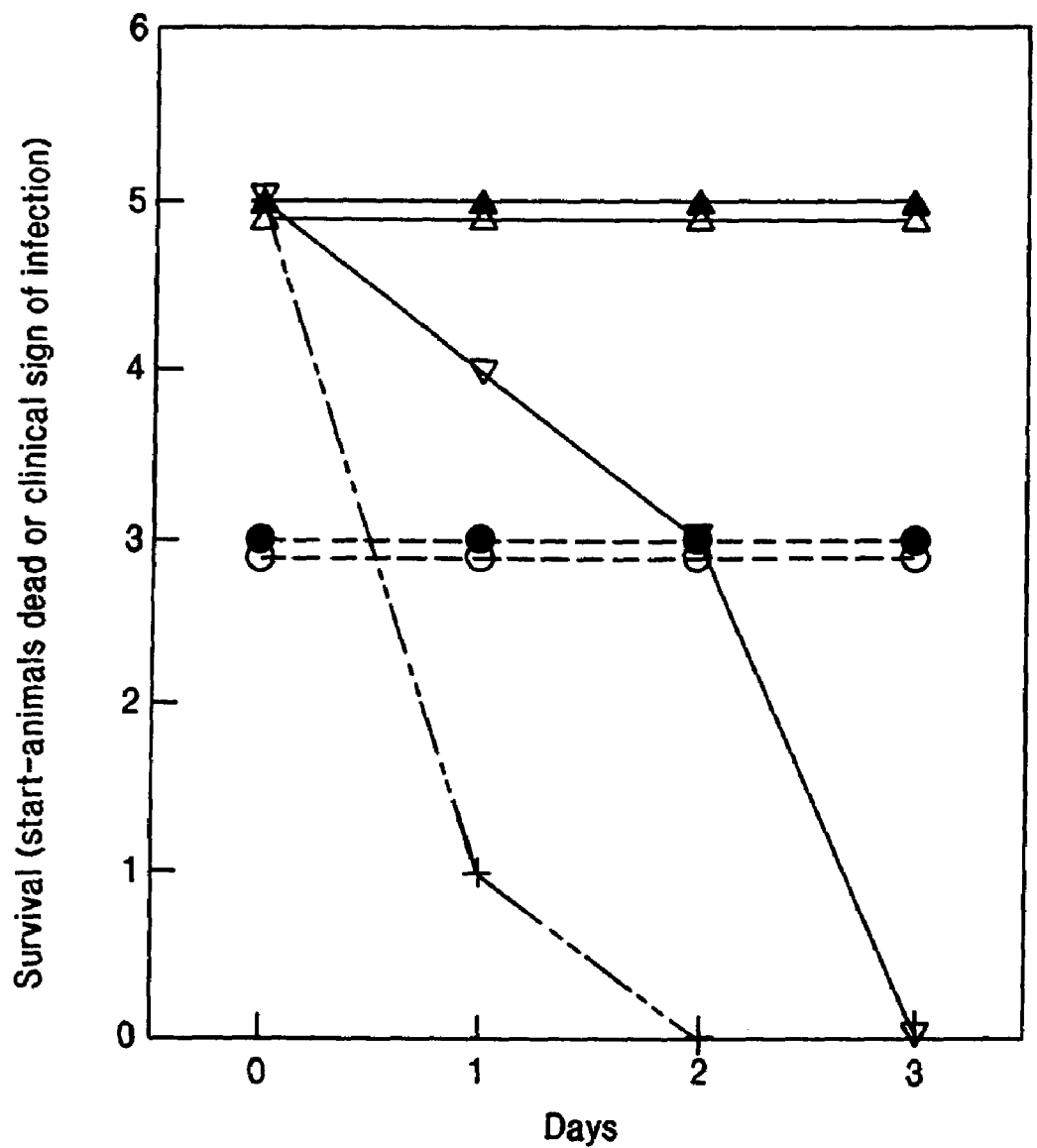
FIG. 2 is a graph indicating the results of an in vivo anti-bacterial activity of deglycosylated pyrrhocoricin (Peptide #1) and (Chex)-Pyrrhocoricin-(Dap (Ac)) (Peptide #21). Three mice per group were used for toxicity (broken lines), and five mice per group were used for efficacy (solid lines). Five additional mice were infected with *E. coli* for negative controls and received 5% dextrose (DS5) instead of test peptides. The results are plotted as Days vs. Survival (which is defined as the time measured from the start of the experiment until the animal is dead or shows clinical signs of infection). The symbols are as follows.

The results are illustrated in FIG. 2. Neither Peptides 1 nor 21 [SEQ ID NOS: 6 and 22, respectively] alone showed any toxicity at 50 mg/kg dose. To assess the success of the infection, five mice were infected with *E. Coli*, but received DS5 instead of test peptides. Two of these control mice died on the third day and the other three became clinically sick, which included decreased activity and head tilt. When the efficacy of the peptides was studied, the Chex-pyrrhocoricin-Dap(Ac) derivative (Peptide 21) protected all 15 mice, regardless of the dose. For unmodified pyrrhocoricin (Peptide 1), the mice that were injected with 10 and 25 mg/kg survived without any clinical signs of disease. However, from the 50 mg/kg group, one mouse died and the other 4 showed clinical signs of disease. This mirrors the drosocin studies in which the peptide was not toxic alone, but became toxic when the mice were infected and became compromised [Hoffmann et al, cited above].

Such an effect was not found for the Chex-pyrrhocoricin-Dap(Ac) peptide. All mice showed some enlargement of the abdominal region during the study, therefore at termination the mice were necropsied. Stomachs and intestines were observed to be enlarged due to the presence of food. There were no other findings. These data indicate that the increase of the proteolytic stability of the pyrrhocoricin peptides compared to drosocin resulted in peptides capable of protecting mice against bacterial infection. The results also warrant further pharmaceutical development with peptides based on Peptide 21 [SEQ ID NO: 22], the Chex-pyrrhocoricin-Dap(Ac) peptide. This analog showed good potency, complete lack of toxicity and similarity in the degradation pathway between human and mouse serum.

EXAMPLE 6

Conformation of Native Pyrrhocoricin

Because native pyrrhocoricin could not be shortened nor could the amino acid composition be changed without a loss of in vitro anti-bacterial activity, it was theorized that the peptide has to assume a certain secondary structure to bind stereospecifically to the target protein. Clearly, this structure is desirably maintained in the design of potential drugs. The bioactive conformations of native glycosylated pyrrhocoricin (Peptide 2) [SEQ ID NO: 2] and its non-glycosylated analog (Peptide 1) [SEQ ID NO: 6] were determined by two-dimensional nuclear magnetic resonance (NMR) spectroscopy.

$^1$H NMR spectra were recorded on a Bruker DMX 750 MHz spectrometer at temperatures in the range 283–298° K. The sample consisted of =600 μg of native glycosylated or non-glycosylated pyrrhocoricin in 125 μL of 50% TFE-d$_3$: 50% H$_2$O solution in a 2.5 mm NMR tube. Two-dimensional TOCSY and NOESY spectra were recorded in the phase sensitive mode using time proportional phase incrementation for quadrature detection in the f1-dimension [D. Marion and K. Wüithrich, *Biochem. Biophys. Res. Comm.*, 113: 967–974 (1983)]. TOCSY spectra were recorded using an MLEV-17 mixing scheme [A. Bax and D. G. Davis, *J. Mag. Res.*, 65:355–360 (1985)] with a mixing times of 80 ms, 16 scans and 512 increments. NOESY spectra were recorded with mixing times of 100 and 300 ms, 64 scans and 512 increments. All 2D spectra were collected over 4096 data points in the f2 dimension, with a spectral width of 9800 Hz in both dimensions. The water proton signal was suppressed using the WATERGATE method, consisting of two sine-shaped gradient pulses on either side of a binomial 3-9-19 pulse of 10 kHz field strength. Spectra were referenced to DSS. The data were processed on a Silicon Graphics (SGI 4D/30) computer using the UXNMR software package. The f1-dimension was zero-filled to 4096 real data points with f1- and f2-dimensions being multiplied by a squared sine function and Gaussian function, respectively, prior to Fourier transformation.

Like the recently published conformation of drosocin [A. McManus et al, cited above], the structure of pyrrhocoricin was largely random coil and there was little change in the backbone conformation upon glycosylation. For pyrrhocoricin, however, there was a subpopulation with organized structure at both the N- and C-termini. FIGS. 3A and 3B summarize the short and medium-range NOEs and show that there were a series of $d_{NN(i,i+1)}$ NOEs present at both the N- and C-termini of the pyrrhocoricins. Additional $d_{\alpha N(i,i+2)}$ NOEs were found in the spectra of the glycosylated derivative.

Taken together, the data indicated the presence of reverse-turns at the pharmacologically important terminal regions. The increase in the turn potential at the termini compared to drosocin may explain the increased in vitro anti-bacterial activity of pyrrhocoricin. A comparison of the αH NMR shifts with random coil values [Merutka et al, *J. Biomol. NMR*, 5:14–24 (1995)] is shown in FIG. 3C. These results suggested that the middle domain of pyrrhocoricin, like drosocin, had an extended structure. Both the unordered-turn conformational equilibrium and the presence of extended regions were further verified by CD spectroscopy (data not shown). Non-glycosylated pyrrhocoricin (Peptide 1) [SEQ ID NO: 6] exhibited a linear unordered reverse turn conformational transition upon going from water to trifluoroethanol as solvents. The CD spectrum of the native glycopeptide recorded in water was more similar to those of unordered peptides (type U spectra). However, the type C spectrum, and therefore the final turn structure was stabilized at a lower trifluoroethanol concentration (50%) for the glycopeptide compared to the non-glycosylated analog, fully supporting the NMR findings. The broadening of the negative band between 210 and 220 nm in the aqueous spectra identified the presence of extended structures for both peptides.

In summary, according to the NMR data the bioactive conformation of pyrrhocoricin involves two reverse-turns at the termini bridged by an extended peptide segment in the middle domain. This hypothetical structure is supported by the antibacterial activity of the cyclic peptide analogs. Cyclization stabilizes reverse-turns, and was expected to improve potency, but the cyclic pyrrhocoricin derivative without expanding the cycle (Peptide 16) [SEQ ID NO: 17] lost activity compared to the analog linear peptide (Peptide 20) [SEQ ID NO: 21], probably due to distortion of the extended domain in the middle of the peptide. When the ring size was increased by repeating an internal octapeptide fragment (Peptide 17) [SEQ ID NO: 18], the resulting cyclic analog became highly active against both gram-negative and gram-positive bacterial strains.

All documents cited above are incorporated by reference herein. This invention is not to be limited in scope by the specific embodiments described herein. Indeed, various modifications of the invention in addition to those described herein will become apparent to those skilled in the art from the foregoing description. Such modifications are intended to fall within the scope of the appended claims. The disclosures of the patents, patent applications and publications cited herein are incorporated by reference in their entireties.

What is claimed is:

1. A modified pyrrhocoricin peptide of the formula R$^1$-SEQ ID NO: 1-R$^2$ having anti-bacterial activity,
   wherein SEQ ID NO: 1 is -Asp-Lys-Gly-Ser-Tyr-Leu-Pro-Arg-Pro-Thr-Pro-Pro-Arg-Pro-Ile-Tyr-Asn-Arg-,
   wherein said Thr in SEQ ID NO: 1 lacks glycosylation;
   wherein the bond between said Asn-Arg amino acids in said SEQ ID NO: 1 improves the stability thereof against protease degradation;
   wherein R$^1$ adds a net positive charge to the N-terminus of said peptide and is selected from the group consisting of
   (a) a straight chain, branched, cyclic or heterocyclic alkyl group;
   (b) a straight chain, branched, cyclic or heterocyclic alkanoyl group;
   (c) a positively charged reporter group;
   (d) a sequence of additional amino acids selected from the group consisting of Arg-Val, Lys-Val, D-Val, Lys-Val-Asp-Lys-Val, wherein the N-terminal additional amino acid is optionally substituted by one or more of (a), (b), or (c); and
   (e) an additional amino acid sequence Arg-Pro-Pro-Thr-Pro-Arg-Pro-Leu-Lys-Val SEQ ID NO: 3 that cyclizes the peptide by bridging between the N- and C-termini thereof; and
   wherein R$^2$ is selected from the group consisting of
   (f) a free hydroxyl, an amide, an imide, or a sugar;
   (g) an additional amino acid selected from the group consisting of Asn, D-Asn, Asp, Asn substituted by a member selected from the group consisting of a free hydroxyl, an amide, an imide, and a sugar; and Asp substituted by a member selected from the group consisting of a free hydroxyl, an amide, an imide and a sugar.

2. The peptide according to claim 1, which is fused to a protein.

3. The peptide according to claim 1, wherein said R$^2$ is an additional amino acid substituted with a modifying sugar or imide.

4. The peptide according to claim 3, wherein R$^2$ is Asn substituted with a sugar.

5. The peptide according to claim 1, wherein said R$^1$ is selected from the group consisting of D-Val-, Arg-Val-, Lys-Val-, and Lys-Val-Asp-Lys-Val- SEQ ID NO: 5.

6. The peptide according to claim 1, wherein said $R^1$ is selected from the group consisting of Acetyl-Arg-Val-, Acetyl-Lys-Val-, and Acetyl-Lys-Val-Asp-Lys-Val-SEQ ID NO: 29.

7. The peptide according to claim 1, wherein said $R^1$ is biotin.

8. The peptide according to claim 1, wherein said $R^1$ is 5(6) carboxyfluorescein.

9. The peptide according to claim 1, wherein $R^1$ is radioactive.

10. The peptide according to claim 1, wherein $R^1$ is -Arg-Pro-Pro-Thr-Pro-Arg-Pro-Leu-Lys-Val-SEQ ID NO: 3, wherein said Val of said $R^1$ is linked to the N-terminal Asp of SEQ ID NO: 1 and the N-terminal amino acid of $R^1$ is linked by a covalent bond to the C-terminal amino acid of $R^2$.

11. The peptide according to claim 1, wherein said $R^1$ provides a detectable signal, upon interaction with other compounds.

12. The peptide according to claim 1 wherein said sugar is selected from the group consisting of 2-acetamido-2-deoxyglucose and triacetyl 2-acetamido-2-deoxyglucose.

13. The peptide according to claim 1, wherein $R^1$ is a D-Val or $R^2$ is a D-Asn.

14. The peptide according to claim 1, wherein the bond between Asn-Arg in SEQ ID NO: 1 is a non-cleavable bond.

15. The peptide according to claim 14, wherein said non-cleavable bond is a thio-amide bond or a reduced amide bond.

16. The peptide according to claim 1, wherein $R^1$ is Acetyl-Lys-Val-Asp-Lys-Val-SEQ ID NO: 29, and $R^2$ is Asn.

17. The peptide according to claim 1, wherein $R^1$ is Acetyl-Arg-Val, and $R^2$ is Asn.

18. The peptide according to claim 1, wherein $R^1$ is Acetyl-Lys-Val, and $R^2$ is Asn.

19. The peptide according to claim 1, wherein $R^1$ is

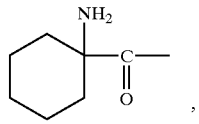

and $R^2$ is Asn.

20. The peptide according to claim 1, wherein $R^1$ is Acetyl-Lys-Val, and $R^2$ is

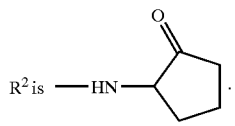

21. The peptide according to claim 1, wherein $R^1$ is Acetyl-Lys-Val, and $R^2$ is

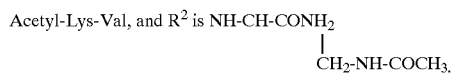

22. The peptide according to claim 1, wherein $R^1$ is Acetyl-Lys-Val, and $R^2$ is Asn-2-acetamido-2-deoxyglucose.

23. The peptide according to claim 1, wherein $R^1$ is Acetyl-Lys-Val, and $R^2$ is Asn-triacetyl-2-acetamido-2-deoxyglucose.

24. The peptide according to claim 1, wherein $R^1$ is D-Val, and $R^2$ is D-Asn.

25. The peptide according to claim 1, wherein $R^1$ is Biotin-Lys-Val, and $R^2$ is Asn.

26. The peptide according to claim 1, wherein $R^1$ is 5(6)-carboxyfluorescein-Lys-Val, and $R^2$ is Asn.

27. The peptide according to claim 1, wherein $R^1$ is Acetyl-Lys-Val, and $R^2$ is Asp.

28. The peptide according to claim 1, wherein $R^1$ is

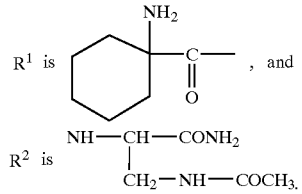

29. The peptide according to claim 1, wherein $R^1$ is Acetyl-Arg-Val, and $R^2$ is

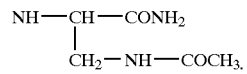

30. The peptide according to claim 1, wherein $R^1$ is a cyclic or heterocyclic alkyl or alkanoyl group.

31. The peptide according to claim 30, wherein said $R^1$ is an amino cycloalkane carboxylic acid.

32. The peptide according to claim 31 wherein said $R^1$ is 1-aminocyclohexane carboxylic acid.

33. The peptide according to claim 1, wherein said $R^2$ amide is an amide of diaminocarboxylic acid.

34. The peptide according to claim 33 wherein said $R^2$ amide is an amide of β-acetyl-2,3-diamino propionic acid.

35. The peptide according to claim 1, wherein said peptide is attached to a carrier.

36. A method of treating a bacterial infection comprising administering to a mammal having said infection an amount of a peptide of claim 1.

37. A method for identifying pharmaceutical compounds comprising:
(i) performing a competitive assay with:
(a) a microorganism susceptible to a peptide of claim 1;
(b) a peptide of claim 1; and
(c) at least one test compound;
(ii) exposing (a) to (b) and (c); and
(iii) identifying said test compound which competitively displaces the binding of said peptide to a receptor on said microorganism.

38. A pharmaceutical composition comprising one or more of the peptides of claim 1 in a pharmaceutically acceptable carrier.

39. A peptide construct having anti-bacterial activity and comprising two peptides, each peptide having the formula $R^1$-SEQ ID NO: 1-$R^2$,
wherein each peptide is linked to the other at the $R^2$ wherein SEQ ID NO: 1 is -Asp-Lys-Gly-Ser-Tyr-Leu-Pro-Arg-Pro-Thr-Pro-Pro-Arg-Pro-Ile-Tyr-Asn-Arg-, wherein the bond between said Asn-Arg amino acids in said SEQ ID NO: 1 improves the stability thereof against protease degradation;

wherein R¹ adds a net positive charge to the N-terminus of said peptide and is selected from the group consisting of (a) a straight chain, branched, cyclic or heterocyclic alkyl group;

(b) a straight chain, branched, cyclic or heterocyclic alkanoyl group;

(c) a positively charged reporter group;

(d) a sequence of additional amino acids selected from the group consisting of Arg-Val, Lys-Val D-Val Lys-Val-Asp-Lys-Val wherein the N-terminal additional amino acid is optionally substituted by one or more of (a), (b), or (c); and wherein R² is selected from the group consisting of (e) a free hydroxyl, an amide, an imide, or a sugar;

(f) an additional amino acid selected from the group consisting of Asn D-Asn, Asp, Asn substituted by a member selected from the group consisting of a free hydroxyl, an amide, an imide, and a sugar, and Asp substituted by a member selected from the group consisting of a free hydroxyl, an amide an imide and a sugar.

40. The peptide construct according to claim 39 wherein R² of each peptide is an amide of an alkanoic acid group and wherein each peptide is linked to the other peptide at R².

41. The peptide construct according to claim 39, comprising two peptides of said formula linked at their R² groups, wherein:

each R¹ is

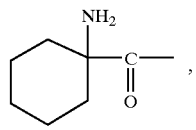

one R² is

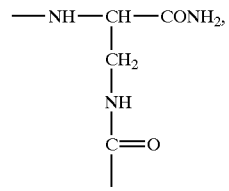

the other R² is —CH—CH₂—NH—COCH₃.

42. The peptide construct according to claim 39, wherein said peptide construct is produced synthetically or recombinantly.

43. The peptide construct according to claim 39, wherein the bond between said Asn-Arg amino acids in SEQ ID NO: 1 is a non-cleavable bond.

44. The peptide construct according to claim 43, wherein said bond is selected from the group consisting of a reduced amide bond and a thioamide bond.

45. The peptide construct according to claim 39, wherein R¹ is a cyclic or heterocyclic alkyl or alkanoyl group.

46. The peptide construct according to claim 45, wherein said R¹ is 1-aminocycloalkane carboxylic acid.

47. The peptide construct according to claim 46, wherein said R¹ is 1-aminocyclohexane carboxylic acid.

48. The peptide construct according to claim 39, wherein said R² amide is an amide of diaminocarboxylic acid.

49. The peptide construct according to claim 39, wherein said R² is an additional amino acid substituted with an amide of diaminocarboxylic acid.

50. The peptide construct according to claim 39, wherein said R² is an additional amino acid substituted with an amide of diaminopropane carboxylic acid.

51. The peptide construct according to claim 39, which is non-glycosylated.

52. The peptide construct according to claim 39, which comprises two peptides linked to one or more diaminocarboxylic acid groups.

53. A pharmaceutical composition comprising the peptide construct of claim 39 in a pharmaceutically acceptable carrier.

54. The composition according to claim 39, wherein said R² of one of said peptides comprises the amide of β-acetyl-2,3-diamino propionic acid and wherein the other peptide is linked to said amide at its carboxyl terminus.

55. A method of treating a bacterial infection comprising administering to a mammal having said infection an amount of a peptide of claim 39.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1701 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..768

(xi) SEQUENCE DESCRIPTION: SEQ ID NO:1:

```
GTG AAT CAG GCA CCG GAG TGC AGG TTC GGG GGT GGA ATC CTT GGG CCG        48
Val Asn Gln Ala Pro Glu Cys Arg Phe Gly Gly Gly Ile Leu Gly Pro
 1               5                  10                  15

CTG GGC AAG CGG CGA GAC CTG GCC AGG GCC AGC GAG CCG AGG ACA GAG        96
Leu Gly Lys Arg Arg Asp Leu Ala Arg Ala Ser Glu Pro Arg Thr Glu
                20                  25                  30

GGC GCG CGG AGG GCC GGG CCG CAG CCC CGG CCG CTT GCA GAC CCC GCC       144
Gly Ala Arg Arg Ala Gly Pro Gln Pro Arg Pro Leu Ala Asp Pro Ala
            35                  40                  45

ATG GAC CCG TTC CTG GTG CTG CTG CAC TCG GTG TCG TCC AGC CTG TCG       192
Met Asp Pro Phe Leu Val Leu Leu His Ser Val Ser Ser Ser Leu Ser
50                  55                  60

AGC AGC GAG CTG ACC GAG CTC AAG TTC CTA TGC CTC GGG CGC GTG GTC       240
Ser Ser Glu Leu Thr Glu Leu Lys Phe Leu Cys Leu Gly Arg Val Val
65                  70                  75                  80

AAG CGC AAG CTG GAG CGC GTG CAG AGC GGC CTA GAC CTC TTC TCC ATG       288
Lys Arg Lys Leu Glu Arg Val Gln Ser Gly Leu Asp Leu Phe Ser Met
                85                  90                  95

CTG CTG GAG CAG AAC GAC CTG GAG CCC GGG CAC ACC GAG CTC CTG CGC       336
Leu Leu Glu Gln Asn Asp Leu Glu Pro Gly His Thr Glu Leu Leu Arg
            100                 105                 110

GAG CTG CTC GCC TCC CTG CGG CGC CAC GAC CTG CTG CGG CGC GTC GAC       384
Glu Leu Leu Ala Ser Leu Arg Arg His Asp Leu Leu Arg Arg Val Asp
        115                 120                 125
```

```
GAC TTC GAG GCG GGG GCG GCG GCC GGG GCC GCG CCT GGG GAA GAA GAC     432
Asp Phe Glu Ala Gly Ala Ala Ala Gly Ala Ala Pro Gly Glu Glu Asp
        130                 135                 140

CTG TGT GCA GCA TTT AAC GTC ATA TGT GAT AAT GTG GGG AAA GAT TGG     480
Leu Cys Ala Ala Phe Asn Val Ile Cys Asp Asn Val Gly Lys Asp Trp
145                 150                 155                 160

AGA AGG CTG GCT CGT CAG CTC AAA GTC TCA GAC ACC AAG ATC GAC AGC     528
Arg Arg Leu Ala Arg Gln Leu Lys Val Ser Asp Thr Lys Ile Asp Ser
                165                 170                 175

ATC GAG GAC AGA TAC CCC CGC AAC CTG ACA GAG CGT GTG CGG GAG TCA     576
Ile Glu Asp Arg Tyr Pro Arg Asn Leu Thr Glu Arg Val Arg Glu Ser
            180                 185                 190

CTG AGA ATC TGG AAG AAC ACA GAG AAG GAG AAC GCA ACA GTG GCC CAC     624
Leu Arg Ile Trp Lys Asn Thr Glu Lys Glu Asn Ala Thr Val Ala His
        195                 200                 205

CTG GTG GGG GCT CTC AGG TCC TGC CAG ATG AAC CTG GTG GCT GAC CTG     672
Leu Val Gly Ala Leu Arg Ser Cys Gln Met Asn Leu Val Ala Asp Leu
    210                 215                 220

GTA CAA GAG GTT CAG CAG GCC CGT GAC CTC CAG AAC AGG AGT GGG GCC     720
Val Gln Glu Val Gln Gln Ala Arg Asp Leu Gln Asn Arg Ser Gly Ala
225                 230                 235                 240

ATG TCC CCG ATG TCA TGG AAC TCA GAC GCA TCT ACC TCC GAA GCG TCC     768
Met Ser Pro Met Ser Trp Asn Ser Asp Ala Ser Thr Ser Glu Ala Ser
                245                 250                 255

TGATGGGCCG CTGCTTTGCG CTGGTGGACC ACAGGCATCT ACACAGCCTG GACTTTGGTT    828

CTCTCCAGGA AGGTAGCCCA GCACTGTGAA GACCCAGCAG GAAGCCAGGC TGAGTGAGCC    888

ACAGACCACC TGCTTCTGAA CTCAAGCTGC GTTTATTAAT GCCTCTCCCG CACCAGGCCG    948

GGCTTGGGCC CTGCACAGAT ATTTCCATTT CTTCCTCACT ATGACACTGA GCAAGATCTT   1008

GTCTCCACTA AATGAGCTCC TGCGGGAGTA GTTGGAAAGT TGGAACCGTG TCCAGCACAG   1068

AAGGAATCTG TGCAGATGAG CAGTCACACT GTTACTCCAC AGCGGAGGAG ACCAGCTCAG   1128

AGGCCCAGGA ATCGGAGCGA AGCAGAGAGG TGGAGAACTG GGATTTGAAC CCCCGCCATC   1188

CTTCACCAGA GCCCATGCTC AACCACTGTG GCGTTCTGCT GCCCCTGCAG TTGGCAGAAA   1248

GGATGTTTTT GTCCCATTTC CTTGGAGGCC ACCGGGACAG ACCTGGACAC TAGGGTCAGG   1308

CGGGGTGCTG TGGTGGGGAG AGGCATGGCT GGGGTGGGGG TGGGGAGACC TGGTTGGCCG   1368

TGGTCCAGCT CTTGGCCCCT GTGTGAGTTG AGTCTCCTCT CTGAGACTGC TAAGTAGGGG   1428

CAGTGATGGT TGCCAGGACG AATTGAGATA ATATCTGTGA GGTGCTGATG AGTGATTGAC   1488

ACACAGCACT CTCTAAATCT TCCTTGTGAG GATTATGGGT CCTGCAATTC TACAGTTTCT   1548

TACTGTTTTG TATCAAAATC ACTATCTTTC TGATAACAGA ATTGCCAAGG CAGCGGGATC   1608

TCGTATCTTT AAAAAGCAGT CCTCTTATTC CTAAGGTAAT CCTATTAAAA CACAGCTTTA   1668

CAACTTCCAT ATTACAAAAA AAAAAAAAAA AAA                                1701
```

(2) INFORMATION FOR SEQ ID NO:2:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:2:

```
Val Asn Gln Ala Pro Glu Cys Arg Phe Gly Gly Gly Ile Leu Gly Pro
 1               5                  10                  15
```

-continued

```
Leu Gly Lys Arg Arg Asp Leu Ala Arg Ala Ser Glu Pro Arg Thr Glu
            20                  25                  30

Gly Ala Arg Arg Ala Gly Pro Gln Pro Arg Pro Leu Ala Asp Pro Ala
            35                  40                  45

Met Asp Pro Phe Leu Val Leu Leu His Ser Val Ser Ser Ser Leu Ser
        50                  55                  60

Ser Ser Glu Leu Thr Glu Leu Lys Phe Leu Cys Leu Gly Arg Val Val
 65                  70                  75                  80

Lys Arg Lys Leu Glu Arg Val Gln Ser Gly Leu Asp Leu Phe Ser Met
            85                  90                  95

Leu Leu Glu Gln Asn Asp Leu Glu Pro Gly His Thr Glu Leu Leu Arg
            100                 105                 110

Glu Leu Leu Ala Ser Leu Arg Arg His Asp Leu Leu Arg Arg Val Asp
            115                 120                 125

Asp Phe Glu Ala Gly Ala Ala Ala Gly Ala Ala Pro Gly Glu Glu Asp
        130                 135                 140

Leu Cys Ala Ala Phe Asn Val Ile Cys Asp Asn Val Gly Lys Asp Trp
145                 150                 155                 160

Arg Arg Leu Ala Arg Gln Leu Lys Val Ser Asp Thr Lys Ile Asp Ser
                165                 170                 175

Ile Glu Asp Arg Tyr Pro Arg Asn Leu Thr Glu Arg Val Arg Glu Ser
            180                 185                 190

Leu Arg Ile Trp Lys Asn Thr Glu Lys Glu Asn Ala Thr Val Ala His
        195                 200                 205

Leu Val Gly Ala Leu Arg Ser Cys Gln Met Asn Leu Val Ala Asp Leu
    210                 215                 220

Val Gln Glu Val Gln Gln Ala Arg Asp Leu Gln Asn Arg Ser Gly Ala
225                 230                 235                 240

Met Ser Pro Met Ser Trp Asn Ser Asp Ala Ser Thr Ser Glu Ala Ser
                245                 250                 255
```